(12) United States Patent
Steinert et al.

(10) Patent No.: US 12,241,820 B2
(45) Date of Patent: Mar. 4, 2025

(54) VISCOMETER AND A METHOD FOR DETERMINING A CONCENTRATION OF A COMPONENT IN A FLUID USING SUCH A VISCOMETER

(71) Applicant: Levitronix GmbH, Zürich (CH)

(72) Inventors: Daniel Steinert, Bülach (CH); Thomas Nussbaumer, Zürich (CH)

(73) Assignee: Levitronix GmbH, Zurich (CH)

( * ) Notice: Subject to any disclaimer, the term of this patent is extended or adjusted under 35 U.S.C. 154(b) by 266 days.

(21) Appl. No.: 17/855,404

(22) Filed: Jun. 30, 2022

(65) Prior Publication Data

US 2023/0031535 A1     Feb. 2, 2023

(30) Foreign Application Priority Data

Jul. 28, 2021   (EP) ...................................... 21188210

(51) Int. Cl.
| | | |
|---|---|---|
| G01N 11/14 | (2006.01) | |
| G01N 33/487 | (2006.01) | |
| H02K 1/14 | (2006.01) | |
| H02K 3/18 | (2006.01) | |

(52) U.S. Cl.
CPC ........... *G01N 11/14* (2013.01); *G01N 33/487* (2013.01); *H02K 1/14* (2013.01); *H02K 3/18* (2013.01)

(58) Field of Classification Search
CPC ...... G01N 11/14; G01N 11/142; G01N 11/16; G01N 2011/147; G01N 33/487; H02K 21/12; H02K 7/09; H02K 7/14; H02K 1/14; H02K 3/18
See application file for complete search history.

(56) References Cited

U.S. PATENT DOCUMENTS

| | | | | |
|---|---|---|---|---|
| 3,722,262 A | * | 3/1973 | Gilinson, Jr. ........ | G01N 11/162 73/54.28 |
| 4,750,351 A | * | 6/1988 | Ball ...................... | G01N 11/08 73/54.04 |

(Continued)

FOREIGN PATENT DOCUMENTS

| | | | | |
|---|---|---|---|---|
| AT | 521097 A1 | * | 10/2019 | ............. G01N 11/14 |
| EP | 1284415 A1 | | 2/2003 | |

(Continued)

OTHER PUBLICATIONS

PuraLev Life Science Integrated Pump Series; c. 2020.

(Continued)

*Primary Examiner* — Andre J Allen
(74) *Attorney, Agent, or Firm* — Global IP Counselors, LLP

(57) ABSTRACT

A viscometer for inline determination of the viscosity of a fluid includes a drive device and a measuring device including a housing and a chamber. The drive device includes a housing in which a stator is arranged. The stator has and having a plurality of coil cores delimited by an end face, and carrying a concentrated winding, and being a bearing and drive stator with which the rotor is magnetically driven without contact and magnetically levitated without contact with respect to the stator. A control device actuates the stator and determines the viscosity based on an operating parameter of the electromagnetic rotary drive.

17 Claims, 18 Drawing Sheets

(56) References Cited

U.S. PATENT DOCUMENTS

| | | | | |
|---|---|---|---|---|
| 5,067,344 | A | * 11/1991 | Fitzgerald | G01N 11/16 73/54.24 |
| 5,157,962 | A | * 10/1992 | Fitzgerald | G01N 11/16 73/54.24 |
| 5,959,196 | A | * 9/1999 | Norcross, Jr. | G01N 11/12 73/54.18 |
| 6,640,617 | B2 | * 11/2003 | Schob | G01N 11/14 73/54.01 |
| 2003/0084708 | A1 | * 5/2003 | Abnett | G01N 11/14 73/54.28 |
| 2019/0356195 | A1 | 11/2019 | Holenstein | |
| 2021/0025800 | A1 | 1/2021 | Schmidegg et al. | |

FOREIGN PATENT DOCUMENTS

| | | | | |
|---|---|---|---|---|
| EP | 2236077 A1 | 10/2010 | | |
| WO | WO-2019183651 A1 | * 10/2019 | | G01N 11/14 |

OTHER PUBLICATIONS

Simon Huwyler, et al.; "Bearingless In-Line Viscometer for the Semiconductor Industry"; Proceedings of IEEE Sensors 2003, IEEE International Conference on Sensors; New Jersey, US; c. 2003; vol. 2; pp. 1077-1081.

\* cited by examiner

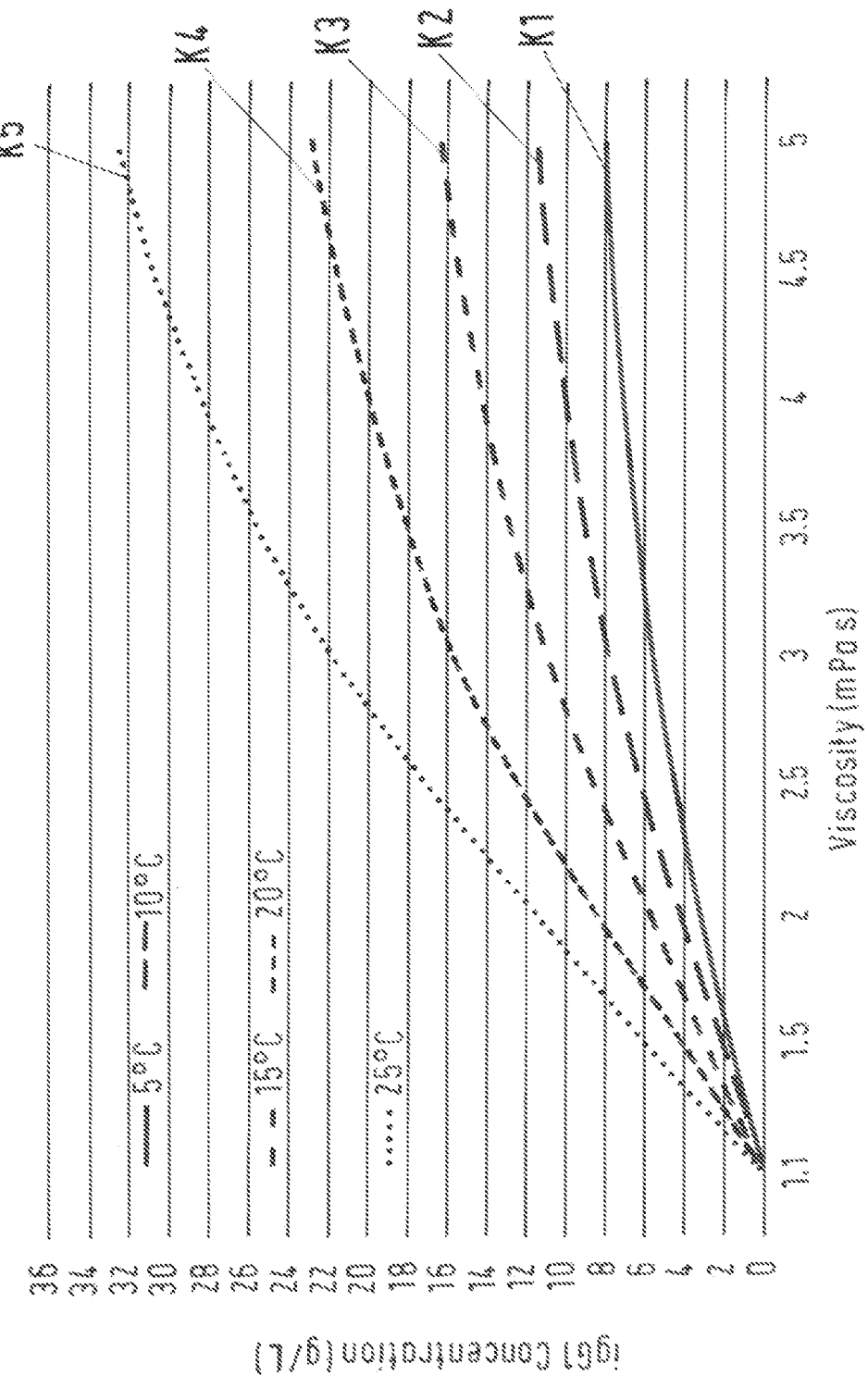

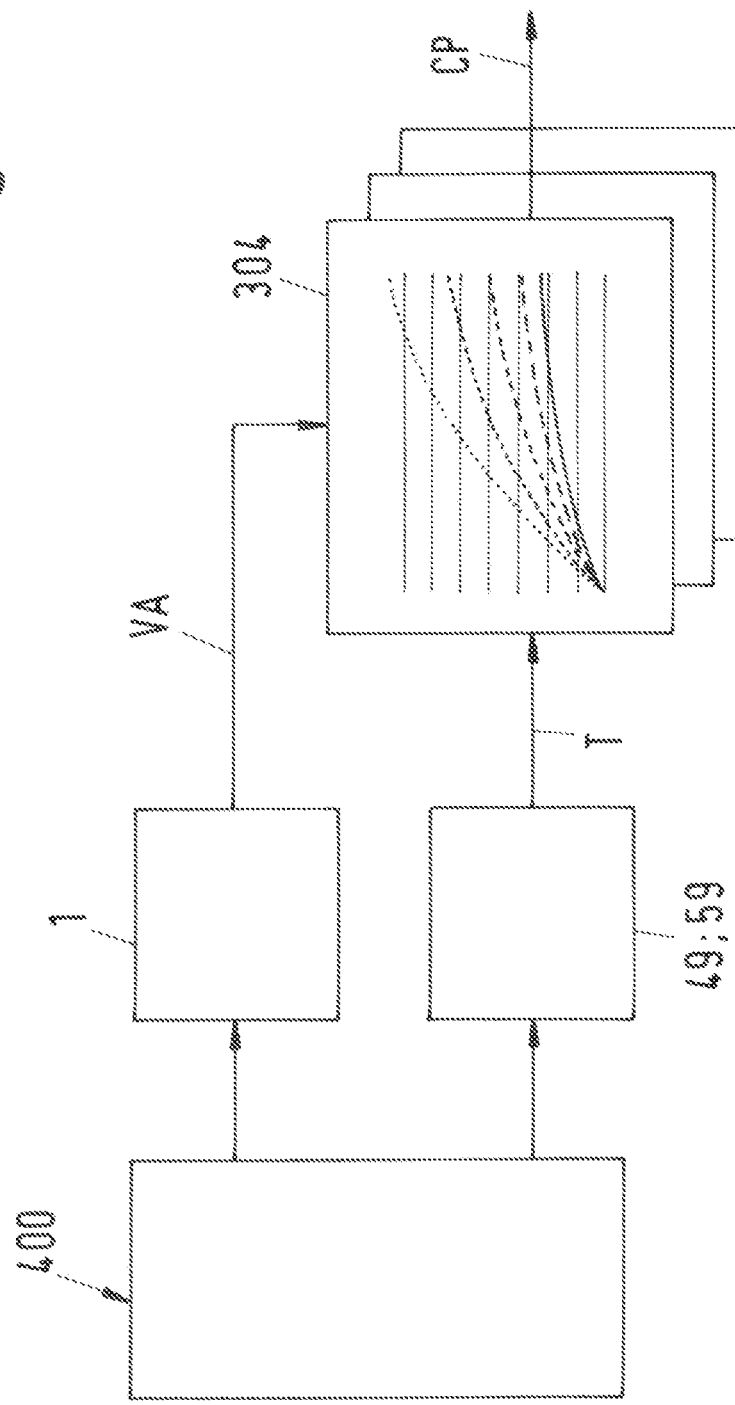

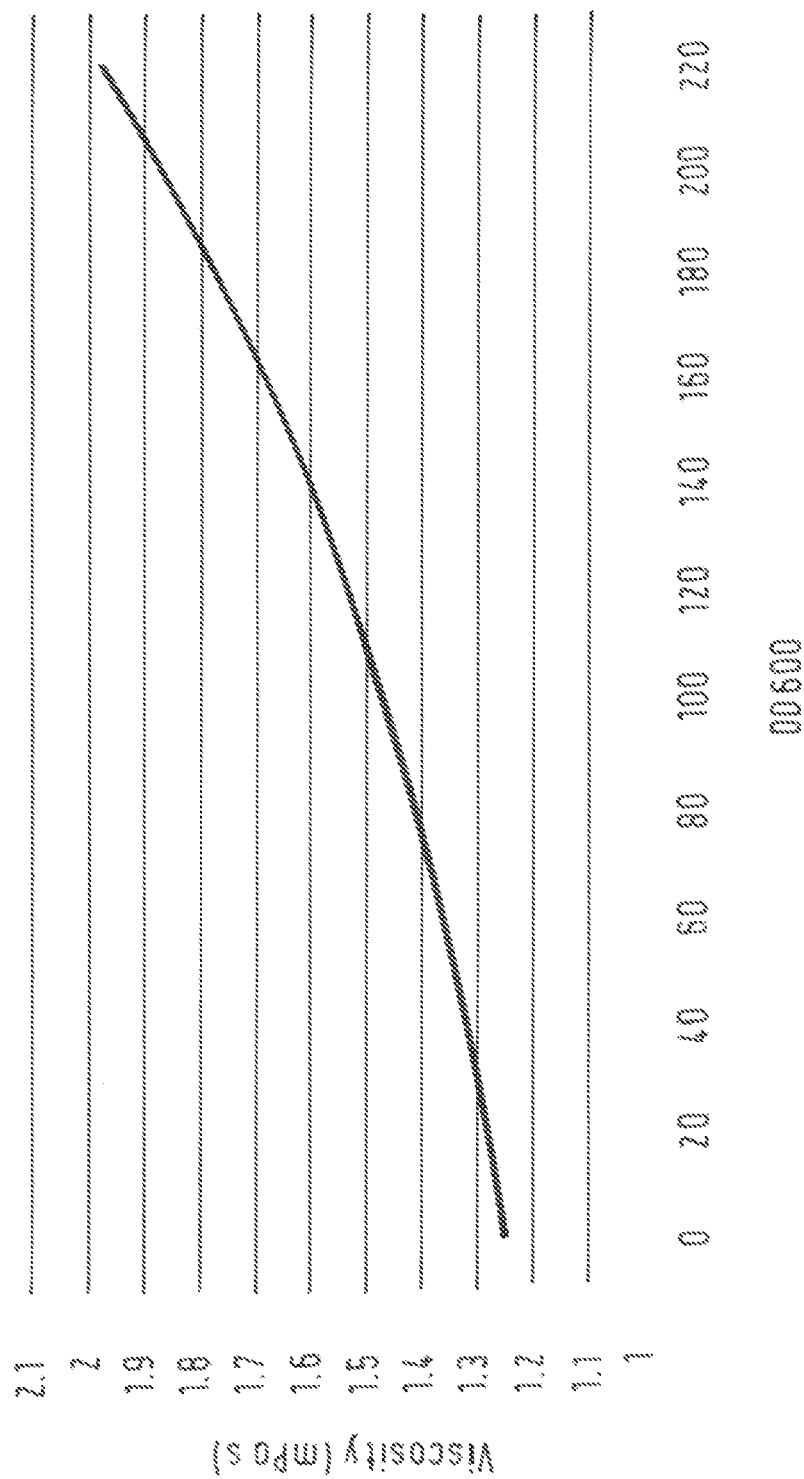

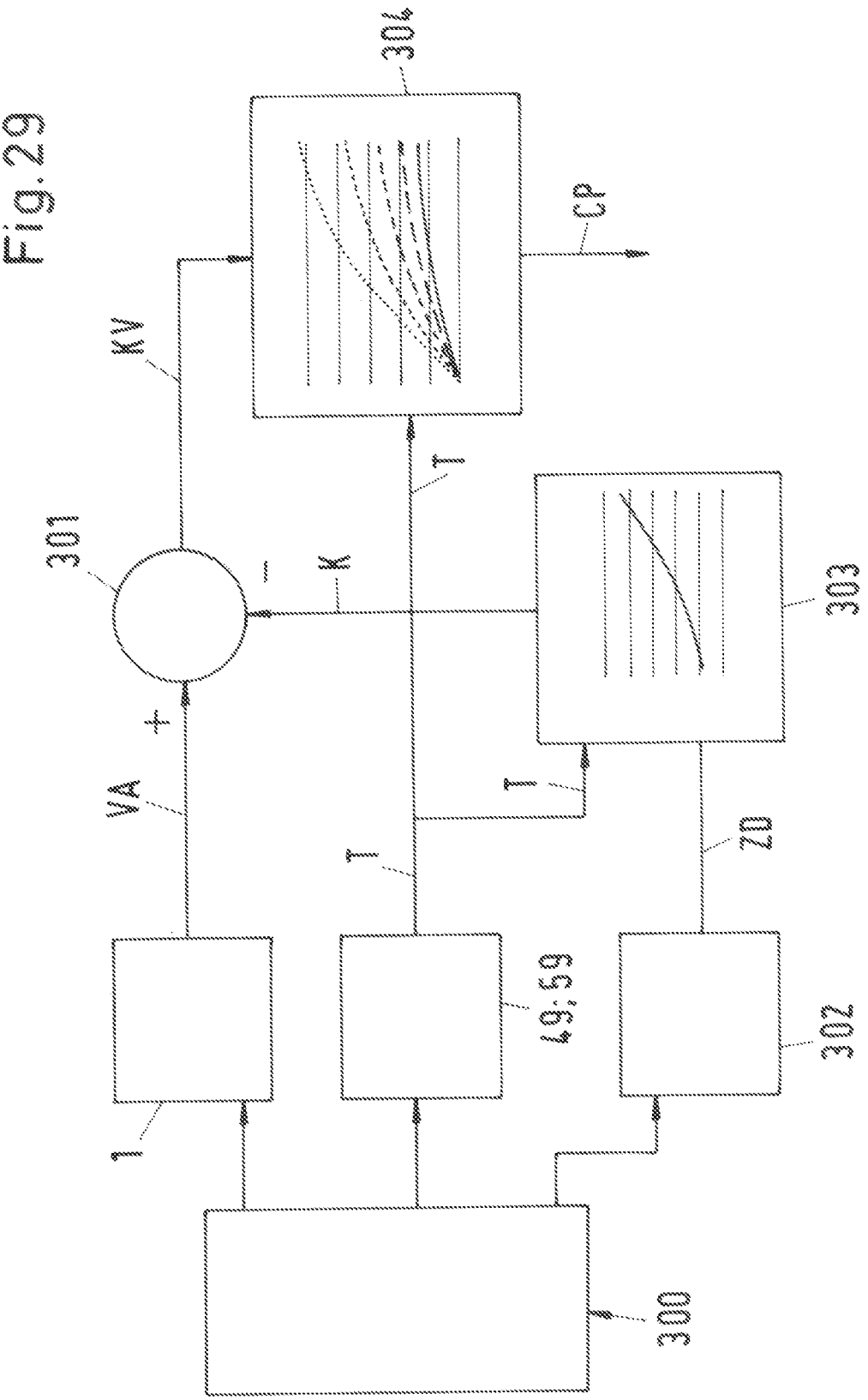

VISCOMETER AND A METHOD FOR DETERMINING A CONCENTRATION OF A COMPONENT IN A FLUID USING SUCH A VISCOMETER

CROSS-REFERENCE TO RELATED APPLICATION

This application claims priority to European Patent Application No. 21188210.5, filed Jul. 28, 2021, the content of which is hereby incorporated in its entirety.

BACKGROUND

Field of the Invention

The disclosure relates to a viscometer for inline determination of the viscosity of a fluid, a single-use device for such a viscometer, and a method for determining a concentration of a component in a fluid.

Background Information

The viscosity of a fluid is generally a measure of the internal friction in a fluid and is in many cases an important parameter by which properties or the condition of a fluid can be analyzed. The dynamic viscosity, usually designated by the letter η, can be considered to be a measure of the toughness of a fluid. Its SI unit is 1 poise, which corresponds to 0.1 Pa·s. In addition to the dynamic viscosity, the kinematic viscosity normalized to the density of the fluid, which is usually designated by the letter v, is also frequently used as a characteristic for a fluid. The kinematic viscosity is therefore the quotient of the dynamic viscosity and the density of the fluid. Within the framework of this application, the term "viscosity" is to be understood as dynamic viscosity, in accordance with common usage.

For many processes, for example in biotechnology or in the pharmaceutical industry, it is often necessary to know or also monitor the viscosity of a fluid, because changes in viscosity have a considerable influence on other characteristics or parameters of the fluid. Considering, for example, a bioreactor in which proteins or other biological substances are produced in a cell broth, the viscosity of the cell broth depends on many factors, such as the temperature, the cell density, or the concentration of the protein(s) in the cell broth. Conversely, conclusions about protein concentrations, e.g., the immunoglobulin concentration or the concentration of extracellular proteins in general, can then be drawn from the actual viscosity, if necessary, with the addition of other parameters. Depending on the process, such information can also serve as a stopping criterion in process monitoring, for example if the concentration of toxins in the cell broth becomes too high.

SUMMARY

It is particularly also desirable for such biotechnological processes that the determination or monitoring of the viscosity to be carried out inline, i.e., in the process itself.

In this way, the very time-consuming regular taking of a sample of the fluid and the subsequent offline determination of the viscosity can be avoided.

Another important criterion in the determination of the viscosity in many applications is the accuracy or reliability of the measurement.

In EP-A-1 284 415, a viscometer is disclosed which enables a very accurate determination of the viscosity, whereby an inline measurement of the viscosity is also possible. The viscometer according to EP-A-1 284 415 comprises an electric rotary drive with a stator having a stator winding and a rotor rotatable in the fluid. In the operating state, the rotor can be driven to rotate magnetically without contact and can be magnetically levitated without contact with respect to the stator. For example, this is realized by designing the electromagnetic rotary drive according to the principle of the bearingless motor. Since the rotor rotates in the fluid whose viscosity is to be determined, the torque required to drive the rotation depends on the viscosity of the fluid.

An important aspect is the contactless levitation and the contactless drive of the rotor because this means that there are no losses in the form of bearing friction or the like. The rotor is completely decoupled mechanically from the rest of the rotary drive, in particular from the stator. Therefore, the electrical drive power to be applied for the rotation of the rotor in the fluid depends substantially only on the viscosity of the fluid. If no or only a negligibly small hydraulic power (pumping power) is provided by the rotor during operation, the current required for torque generation depends only on the internal friction and thus on the viscosity of the fluid. Thus, the viscosity of the fluid can be determined from the electric current required to generate the torque that drives the rotation of the rotor and the rotational speed (rotational frequency) of the rotor.

If the hydraulic power of the rotor is negligibly small, the viscosity of the fluid is directly proportional to the torque-generating current at a constant rotational frequency of the rotor.

If the hydraulic power of the rotor is not negligible, it can be determined, for example, by a flow measurement and a measurement of the pressure difference generated. The hydraulic power is then subtracted from the electrical drive power, and the viscosity of the fluid can then be determined from the remaining power.

In particular, if the electromagnetic rotary drive is designed according to the principle of the bearingless motor, the operation is made by magnetic rotary fields and a field-oriented drive control (vector control). In this case, the torque-generating current can be determined in a simple manner.

Even though the viscometer disclosed in EP-A-1 284 415 has proven itself very well in practice, it has been determined that there is still room for improvement.

For example, in the biotechnology industry, today, in addition to high measuring accuracy, the aim is also to adapt all devices to the respective process very quickly and easily. This then also requires the fastest possible interchangeability, as well as a simple and as uncomplicated as possible handling and provision of the individual components, naturally under the condition that no concessions to process reliability or to the very high cleanliness requirements are necessary.

Starting from this state of the art, it is therefore an object of the present disclosure to propose a viscometer for inline determination of the viscosity of a fluid, which can be handled in a very simple manner and also allows a high measurement accuracy. In addition, it is an object of this disclosure to propose a method for determining a concentration of a component in a fluid, which can be performed with such a viscometer.

The subject matters of this disclosure meeting these objects are characterized by the features of the embodiments disclosed herein.

According to an embodiment of the invention, a viscometer for inline determination of the viscosity of a fluid is thus proposed, with a drive device and with a measuring device, wherein the measuring device comprises a measuring housing with an inlet and with an outlet for the fluid, as well as a measuring chamber in which a rotor having a ring-shaped or disk-shaped magnetically effective core is provided, wherein the drive device comprises a drive housing in which a stator is arranged, which cooperates with the rotor as an electromagnetic rotary drive, wherein the stator has a plurality of coil cores, each of which is delimited by an end face, and each of which carries at least one concentrated winding, wherein the stator is designed as a bearing and drive stator with which the rotor can be magnetically driven without contact about an axial direction in the operating state, and with which the rotor can be magnetically levitated without contact with respect to the stator, and wherein a control device for actuating the stator and for determining the viscosity on the basis of an operating parameter of the electromagnetic rotary drive is further provided in the drive housing. The measuring device is designed to be inserted into the drive device such that the end faces of the coil cores are arranged around the magnetically effective core of the rotor, wherein the measuring housing can be detachably connected to the drive housing so that the measuring housing and the drive housing can be fixed relative to each other and separated from each other.

It is a substantial aspect of the viscometer according to an embodiment of the invention that the viscometer comprises two devices which can be separated from each other, namely a measuring device with a measuring housing and a drive device with a drive housing, wherein the measuring device can be connected to and fixed to the drive device in a simple manner, namely by inserting the measuring housing into the drive housing.

Preferably, the measuring device comprises all components that come into contact with the fluid during the measuring process, while the components of the drive device do not come into contact with the fluid. Thus, for example, after a process has been terminated, it is possible to separate the measuring device from the drive device, to clean and/or to sterilize it, and then reinsert it into the drive device so that the viscometer is ready for a new measurement or for a new process. Here, in particular, it is advantageous that no modifications or cleaning work are required on the drive device, only the measuring device has to be treated and then reinserted in the drive device.

This makes the viscometer particularly easy to handle.

According to a particularly preferred embodiment, the measuring device is designed as a single-use device for single use, and the drive device is designed as a reusable device for multiple use. The term "single-use device" means that the device is designed for single use, i.e., it can only be used once as intended and must then be replaced by a new, not yet used single-use device. For a measurement or for a process, a still unused measuring device is then simply inserted into the drive device and fixed to it. After termination of the measurement or process, the measuring device designed as a single-use device is separated from the drive device, and can then be disposed of.

According to a preferred embodiment, the electromagnetic rotary drive, which comprises the rotor and the stator, is designed as a temple motor, and each coil core comprises a bar-shaped longitudinal leg which extends from a first end in the axial direction to a second end, and a transverse leg which is arranged at the second end of the longitudinal leg and which extends in a radial direction that is perpendicular to the axial direction, wherein each transverse leg is delimited by one of the end faces, and wherein at least one of the concentrated windings is arranged on each longitudinal leg, which surrounds the respective longitudinal leg. This embodiment as a temple motor is particularly compact and space-saving.

According to a preferred embodiment, the measuring housing can be fixed to the drive housing or can be detached from the drive housing by a rotation relative to the drive housing and about the axial direction. For this purpose, the connection and fixing between the measuring housing and the drive housing can be designed, for example, as a bayonet connection or a bayonet lock.

According to a further preferred embodiment, the drive device comprises a connecting means or device which is designed to be rotatable with respect to the drive housing between an open position and a closed position, wherein the measuring device can be inserted into the drive device and can be separated from the drive device when the connecting means is in the open position, and wherein the measuring housing and the drive housing are fixed relative to each other when the connecting means is in the closed position. This embodiment has the advantage that the measuring housing which comprises the inlet and the outlet for the fluid, does not have to be rotated to connect to and to separate from the drive housing. In particular, when the viscometer is integrated into fluid systems, it can be an advantage if no rotation of the inlet and the outlet, in particular about the axial direction, is necessary to insert or remove the measuring device.

Preferably, the measuring device comprises a storage unit in which calibration data for the measuring device are stored, wherein the drive device comprises an interface via which data from the storage unit can be transmitted to the control device. In particular for measurements that require a very high precision, it is often necessary that the viscometer is calibrated. For this purpose, the measuring device should then usually be calibrated together with the drive device. If the measuring device, which is designed as a single-use device, for example, is now replaced by a new measuring device, it could be necessary to recalibrate the viscometer, which now comprises this new measuring device—inserted into the drive device. For example, minute variations in the geometric dimensions of components of the measuring device, such as minute variations in the outer diameter of the rotor or in its magnetic properties, can result in the need for a new calibration after the measuring device has been replaced. Such variations are, for example, due to manufacturing technology and are usually unavoidable, at least not at a reasonable effort.

To solve this problem, for example, each measuring device in a reference viscometer can be calibrated with a reference drive device. The resulting calibration data specific to the respective measuring device is then stored in the storage unit of this measuring device. If this measuring device is now inserted into the drive device, the specific calibration data is transmitted to the control unit of the drive device via the interface, so that it is no longer necessary to recalibrate the viscometer after replacing the measuring device.

In particular for the design of the measuring device as a single-use device, it is preferred that the storage unit is gamma-stable, by which is meant that the storage unit is not damaged during a gamma sterilization, so that in particular no calibration data is lost. This is because it is advantageous if the single-use device, for example the measuring device, can be gamma-sterilized. In this type of sterilization, the component to be sterilized is exposed to gamma radiation.

The advantage of gamma sterilization, for example in comparison with steam sterilization, is in particular that sterilization can also take place through the packaging. For single-use parts or single-use devices in particular, it is a common practice that the parts are placed in the packaging after they are manufactured and then stored for a period of time before being shipped to the customer. In such cases, sterilization takes place through the packaging, which is not possible with steam sterilization or other processes.

Another advantage of gamma sterilization compared to steam sterilization is that gamma sterilization does not have to be performed at a high or elevated temperature. Steam sterilization, on the other hand, must be performed at a high temperature. Due to the high temperature, there is a risk that plastic components of the single-use device in particular can be destroyed or damaged. For example, plastic components can warp, which can change important or critical dimensions of the components.

Gamma-stable storage units used in this sense can be, for example: FRAM (Ferroelectric Random Access Memory), RFID elements (RFID: Radio Frequency Identification), or optoelectronically readable elements such as barcodes or two-dimensional codes, e.g. QR codes (QR: Quick Response).

Furthermore, it is possible to determine calibration data for the drive device as well, which is determined, for example, by a calibration with a reference measuring device. The calibration data for the drive device is then preferably saved or stored in the control device of the respective drive device.

According to a particularly preferred embodiment, the magnetically effective core of the rotor comprises a permanent magnet for generating a rotor magnetic field, wherein the drive device comprises at least one magnetic field sensor with which the rotor magnetic field can be determined.

The rotor magnetic field generated by the permanent magnet is guided from the magnetically effective core of the rotor through the air gap between the rotor and the stator mainly through the end faces of the coil cores into the coil cores, through the coil cores, and then back again into the magnetically effective core of the rotor. If there are now changes in the rotor magnetic field, this can also lead to changes in the torque that drives the rotation of the rotor. However, since this torque is the basis for determining the viscosity, changes in the rotor magnetic field can also lead to changes in the viscosity measurement. Such changes in the rotor magnetic field can be temperature-related, for example. If, for example, the fluid flowing through the measuring device increases the temperature of the rotor, this results in a decrease in the rotor magnetic field, or more precisely, a decrease in the field strength of the rotor magnetic field.

The actual strength of the rotor magnetic field can be determined with the at least one magnetic field sensor in the drive device. If there are now changes in the rotor magnetic field, this can be determined by the magnetic field sensor and an appropriate correction can be made so that the determination of the viscosity is not falsified by the change in the rotor magnetic field. The correction values required for this can be saved or stored in the control device, for example in the form of a lookup table or in the form of a polynomial function.

Particularly preferably, at least one radial magnetic field sensor is provided, with which a radial component of the rotor magnetic field can be determined, and also preferably at least one axial magnetic field sensor, with which an axial component of the rotor magnetic field can be determined.

Since the magnetic flux in the air gap between the rotor and the stator is mainly in the radial direction, radial magnetic field sensors are particularly suitable for detecting even smaller changes in the rotor magnetic field.

The axial magnetic field sensor is particularly advantageous if the position of the rotor is passively magnetically stabilized with respect to the axial direction, which is a particularly preferred embodiment. In this case, the asymmetry in the flow of the fluid around the rotor can lead to the fact that the position of the rotor changes with respect to the axial direction. Usually, the fluid flows mainly over the upper side of the rotor and only a significantly smaller part of the fluid flows below the rotor, resulting in the mentioned asymmetry. If there is now a change in the flow of the fluid through the measuring device, for example by an increase in the flow rate, this can lead to a displacement of the rotor in the axial direction. Such an axial displacement usually leads to a change in the rotor magnetic field, which in turn can then lead to a change in the viscosity measurement. Such a displacement of the rotor in the axial direction can be detected with the axial magnetic field sensor, and in particular the direction of the displacement, i.e., upwards, or downwards, can also be determined. As a consequence, changes in the axial position of the rotor can be detected and taken into account when determining the viscosity.

If several radial magnetic field sensors and at least one axial magnetic field sensor are provided, it is also possible to determine the axial magnetic field sensor only for determining the sign of the axial displacement, i.e., whether the rotor is displaced upwards or downwards with respect to the axial direction. The amplitude of the axial displacement, i.e., the amount by which the rotor is displaced with respect to the axial direction, can be determined from the signals of the radial magnetic field sensors. Determining the amplitude of the axial displacement with the help of the radial magnetic field sensors has the advantage that, in particular in the case of several symmetrically or pairwise symmetrically arranged radial magnetic field sensors, the influence of tilting of the rotor or the influence of other field disturbances of the magnetic field is compensated, thus increasing the accuracy of the determination of the axial position of the rotor.

It is a further preferred measure that the measuring device comprises a temperature sensor with which the temperature of the fluid can be determined in the measuring device. Since for very many fluids the viscosity depends significantly on the temperature, it is advantageous if the temperature of the fluid is determined there, where the viscosity is also determined, namely in the measuring device. In many applications, this is more accurate than a determination of the temperature of the fluid outside the measuring device.

According to a particularly preferred embodiment, the measuring chamber in which the rotor is arranged is designed as a protuberance in a bottom of the measuring housing, wherein, with respect to the normal position of use, a main flow connection for the fluid is provided in the axial direction above the measuring chamber between the inlet and the outlet, through which main flow connection the fluid can flow from the inlet to the outlet.

Here, such embodiments are preferred, in which a flow guiding element is provided in the main flow connection, which is arranged centrally above the rotor, and which is designed to divide the fluid into a first partial flow and into a second partial flow in such a way that the flow guiding element between the inlet and the outlet has the first partial flow flowing around it on one side and the second partial flow flowing around it on the other side. Due to the flow guiding element, which covers a central area of the rotor, the fluid is divided into the two partial flows in the operating state, which only flow over the periphery of the surface of the rotor. In this way, rotational flows in the main flow connection are prevented or at least drastically reduced by the flow guiding element. Such rotational flows can have a negative effect because they flow against the main flow on one side at the surface of the rotor and flow in the same direction as the main flow on the other side. This can lead to asymmetric friction effects, which can have a negative effect on the measurement of the viscosity.

A further advantage of the embodiment with the flow guiding element is that it occupies a significant space in the main flow connection. This has the advantage that the wet volume, by which is meant the area of the measuring device which is filled with the fluid or through which the fluid flows, is reduced. This is a particularly important aspect if the fluid is a very valuable or expensive fluid.

It is a further preferred measure that the flow guiding element has a plurality of side channels which divert a portion of the fluid from the main flow connection in the axial direction towards the rotor. Due to this measure, the secondary flow can be amplified, which is the flow of the fluid that flows around the rotor and is therefore a substantial factor in determining the viscosity.

As already mentioned, it is a particularly preferred embodiment that the drive device is designed as a reusable device for multiple use, and the measuring device is designed as a single-use device for single use.

Furthermore, a single-use device for single use is proposed by an embodiment of the invention, wherein the single-use device is designed as a measuring device for a viscometer according to an embodiment of the invention.

Furthermore, a method for determining a concentration of a component in a fluid is proposed by an embodiment of the invention, characterized by the following steps:
  Providing a viscometer which is designed according to an embodiment of the invention,
  Providing a relationship between the concentration of the component in the fluid and the viscosity of the fluid,
  Determining the viscosity of the fluid by the viscometer,
  Determining the concentration from the relationship between the concentration and the viscosity.

Since the viscometer according to an embodiment of the invention enables a very simple, precise and easy-to-handle determination of the viscosity, it is also particularly suitable for determining characteristic values, properties or states of a fluid which can be determined with the help of the viscosity of the fluid. One important of these values is the concentration of a component in a fluid. Such concentration determinations also play an important role in the biotechnology and pharmaceutical industries in particular. In this context, the concentrations of proteins in a bioreactor or in a cell broth, for example, can be mentioned as examples. One important application is, for example, the determination of the immunoglobulin (antibody) concentration in a fluid. Especially the determination of the concentration of immunoglobulins G (IgG) plays a significant role in modern diagnostics, in biotechnology and in the development of vaccines and drugs.

According to a preferred embodiment of the method according to the invention, a protein concentration in a cell broth is determined, wherein an actual viscosity of the cell broth is determined with the viscometer, wherein, preferably photometrically, an actual cell density in the cell broth is determined, wherein a correction value for the viscosity is determined on the basis of a reference value for the relationship between the cell density and the viscosity, wherein a corrected viscosity is determined from the actual viscosity and the correction value, and wherein the protein concentration in the cell broth is determined from the corrected viscosity and the relationship between the concentration and the viscosity.

Further advantageous measures and embodiments of the invention are described herein.

BRIEF DESCRIPTION OF THE DRAWINGS

Embodiments of the invention will be explained in more detail hereinafter with reference to the drawings.

FIG. 26 illustrates a diagram showing the relationship between the concentration of an immunoglobulin and the viscosity for different temperatures, FIG. 27 illustrates a schematic representation of a first embodiment of a method according to the invention, in which a protein concentration is determined, FIG. 28 illustrates a diagram showing the relationship between the cell density in a cell suspension and the viscosity of the cell suspension, and FIG. 29 illustrates a schematic representation of a second embodiment of a method according to the invention.

DETAILED DESCRIPTION

Figure 1:
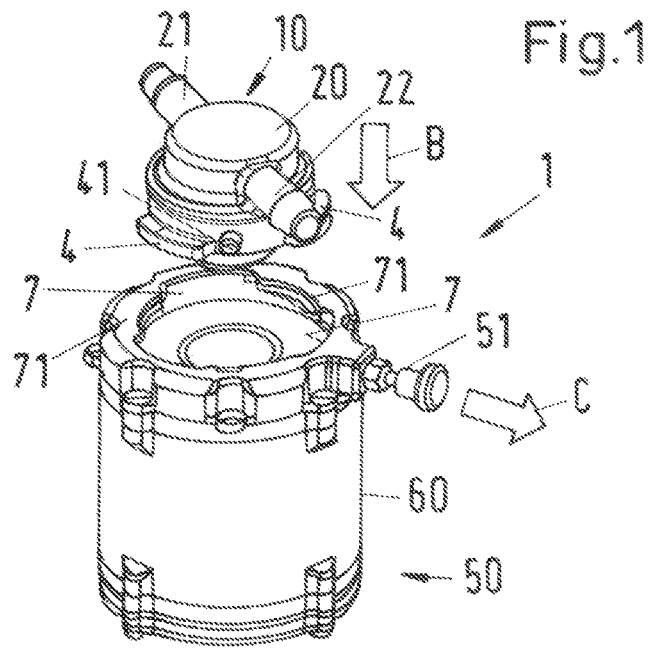
FIG. 1 illustrates a first embodiment of a viscometer according to the invention in a perspective view.

FIG. 1 shows a perspective representation of a first embodiment of a viscometer according to an embodiment of the invention, which is designated as a whole by the reference sign 1. The viscometer 1 comprises a measuring device 10 with a measuring housing 20, and a drive device 50 with a drive housing 60. As will be described in more detail, the measuring device 10 and the drive device 50 are designed in such a way that they can be assembled and separated from each other in a simple manner. Particularly preferably, this assembly and separation is possible by hand and in particular without tools.

The measuring device 10 is designed to be inserted into the drive device 50, wherein the measuring housing 20 can be detachably connected to the drive housing 60 so that the measuring housing 20 and the drive housing 60 can be fixed relative to each other and separated from each other. The assembly of the measuring device 10 and the drive device 50 will be explained later with reference to FIG. 2 and FIG. 3.

Figure 4:
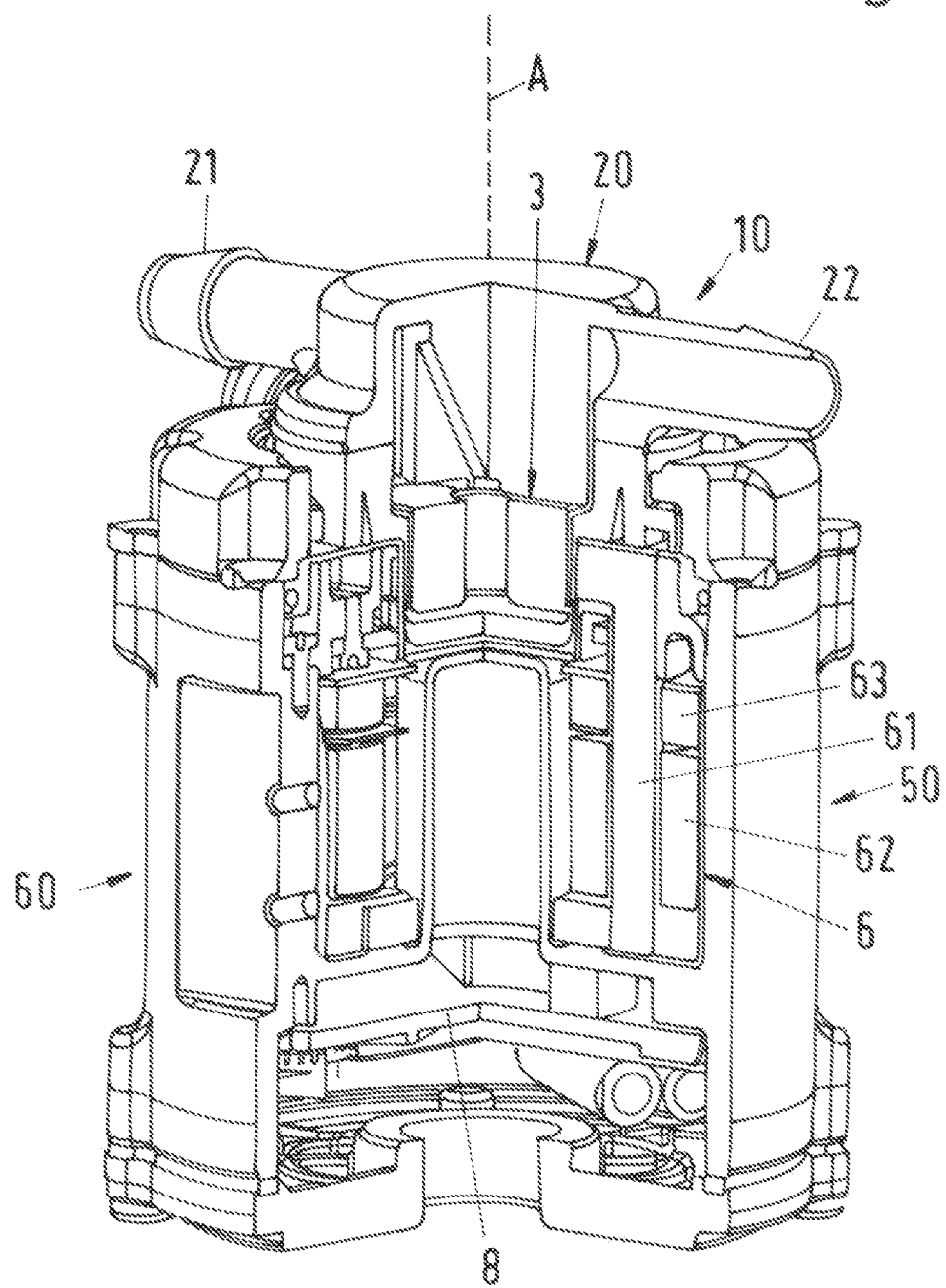
FIG. 4 illustrates a perspective sectional representation of the first embodiment.

FIG. 4 shows a perspective sectional representation of the first embodiment of the viscometer 1, wherein a quarter of the viscometer 1 is cut out.

Figure 5:
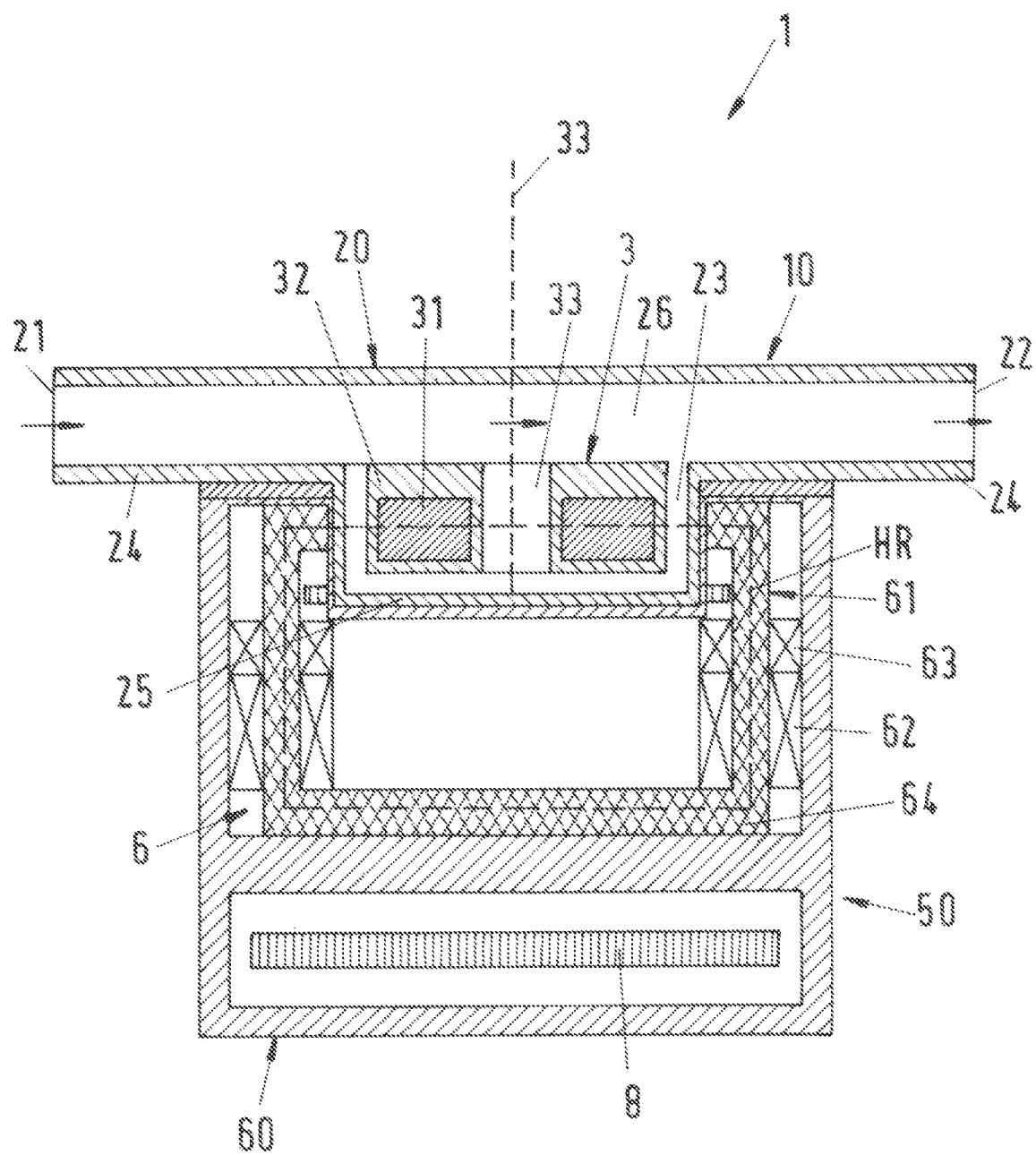
FIG. 5 illustrates a schematic sectional representation of the first embodiment in a section along the axial direction.

For a better understanding, FIG. 5 still shows in a schematic representation a section through the viscometer 1 in a section along an axial direction.

Figure 6:
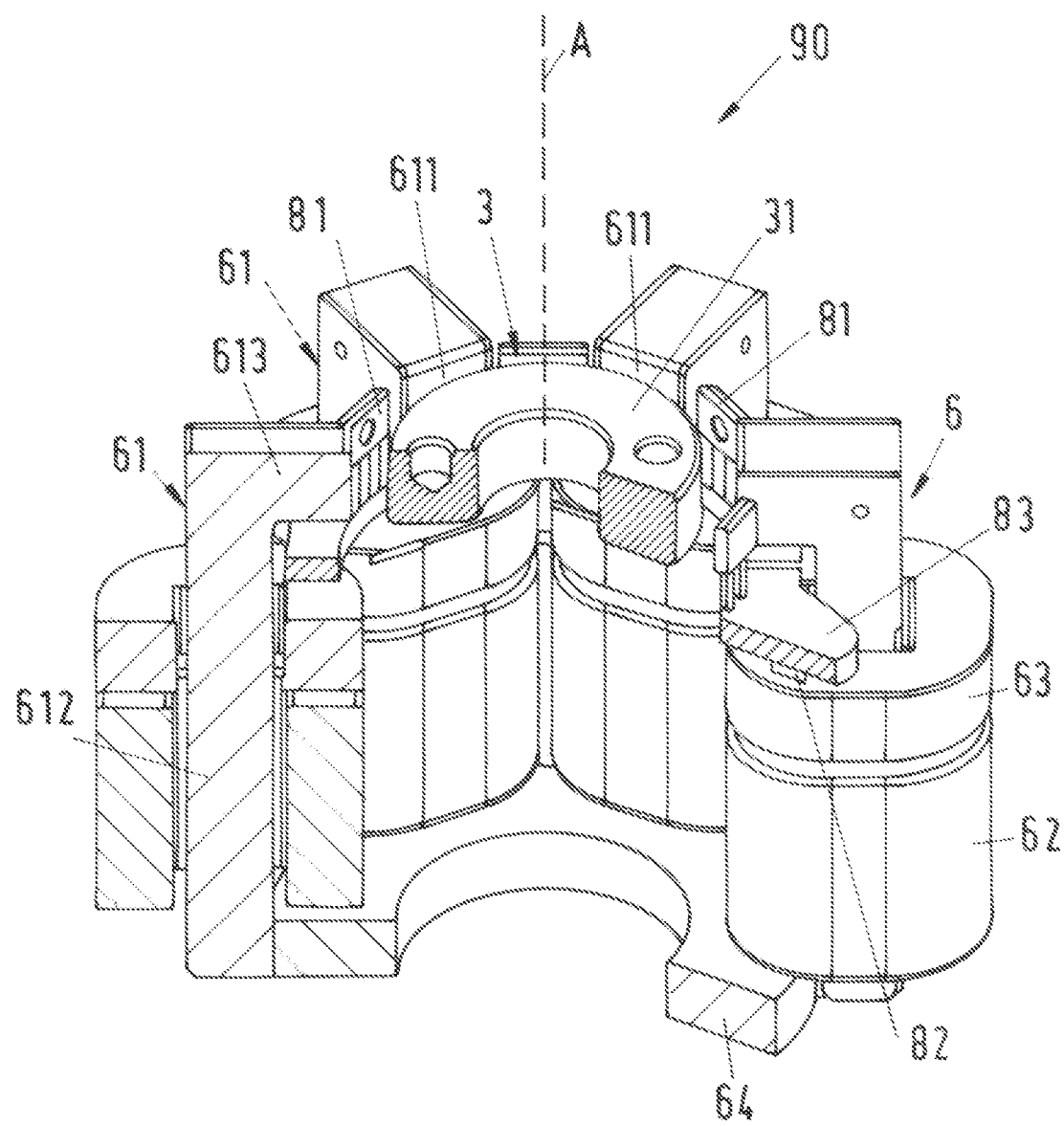
FIG. 6 illustrates a perspective sectional representation of the electromagnetic rotary drive of the first embodiment.

The viscometer 1 according to an embodiment of the invention is based on the fact to determine the viscosity of a fluid on the basis of an operating parameter of an electromagnetic rotary drive 90. FIG. 6 shows in a perspective sectional representation the electromagnetic rotary drive 90 of the first embodiment of the viscometer 1.

The measuring housing 20 of the measuring device 10 has an inlet 21 and an outlet 22 for the fluid, as well as a measuring chamber 23 (FIG. 5) in which a rotor 3 having a ring-shaped or disk-shaped magnetically effective core 31 is provided. The magnetically effective core 31 is designed in a permanent magnetic manner. For this purpose, the magnetically effective core 31 can comprise at least one permanent magnet, but also several permanent magnets, or—as in the embodiment described here—can consist entirely of a permanent magnetic material, so that the magnetically effective core 31 is the permanent magnet. The permanent magnet, which forms the magnetically effective core 31, is designed in a ring-shaped manner and is magnetized in a diametrical direction, i.e., perpendicular to the axial direction A. The permanent magnet generates a rotor magnetic field, which is illustrated in FIG. 5 by the dashed line with the reference sign HR.

Those ferromagnetic or ferrimagnetic materials, which are magnetically hard, that is which have a high coercive field strength, are typically called permanent magnets. The coercive field strength is that magnetic field strength which is required to demagnetize a material. Within the framework of this application, a permanent magnet is understood as a component or a material, which has a coercive field strength, more precisely a coercive field strength of the magnetic polarization, which amounts to more than 10,000 A/m.

The measuring chamber 23 in which the rotor 3 is arranged is designed as a protuberance 25 in a bottom 24 of the measuring housing 20. With respect to the normal position of use which is represented in FIGS. 1 to 6, a main flow connection 26 is provided in the axial direction A above the measuring chamber 23 between the inlet 21 and the outlet 22, through which main flow connection 26 the main flow of the fluid can flow from the inlet 21 to the outlet 22, as indicated by the arrows without reference signs in FIG. 5. With respect to the axial direction A, the measuring chamber is arranged below the main flow connection 26 so that the rotor 3 is overflowed by the main flow of the fluid in the operating state.

A stator 6 is arranged in the drive housing 60 of the drive device 50, which cooperates with the rotor 3 as the electromagnetic rotary drive 90, wherein the stator 6 has a plurality of coil cores 61, each of which is delimited by an end face 611 (see FIG. 6) and each of which carries at least one concentrated winding 62, 63.

Furthermore, a control device 8 for actuating the stator 6 and for determining the viscosity on the basis of an operating parameter of the electromagnetic rotary drive 90 is provided in the drive housing 60. The control device 8 is arranged in the drive housing 60 at the lower end of the drive housing 60 as represented (FIG. 5).

The drive device 50 and the measuring device 10 with the rotor 3 arranged in the measuring chamber 23 are designed such that the end faces 611 of the coil cores 61 are arranged around the magnetically effective core 31 of the rotor 3 when the measuring device 10 is inserted into the drive device 50. Thus, the protuberance 25 and the drive housing 60 are dimensioned such that the protuberance 25 can be inserted into a recess of the drive housing 60 in such a way that the end faces 611 of the coil cores 61 are arranged around the magnetically effective core 31 of the rotor 3.

In the following, the electromagnetic rotary drive 90 is now explained in more detail.

The electromagnetic rotary drive 90 (see FIG. 6) is designed as a temple motor and comprises the stator 6, which has the plurality of coil cores 61—here six coil cores 61—each of which comprises a longitudinal leg 612 extending in the axial direction A, and a transverse leg 613 arranged perpendicular to the longitudinal leg 612 extending in a radial direction and delimited by the end face 611. The coil cores 61 are arranged equidistantly on a circular line so that the end faces 611 surround the rotor 3 of the electromagnetic rotary drive 90 when the measuring device 10 is inserted into the drive device 50. Two concentrated windings 62, 63 are arranged on each longitudinal leg 612, surrounding the respective longitudinal leg 612, namely a drive coil 62 and a control coil 63.

The rotor 3 is magnetically levitated without contact with respect to the stator. Furthermore, the rotor 3 can be magnetically driven without contact by the stator 6 for rotation about a desired axis of rotation. The desired axis of rotation refers to that axis about which the rotor 3 rotates in the operating state when the rotor 3 is in a centered and not tilted position with respect to the stator 6, as is represented in FIG. 6, for example. This desired axis of rotation defines the axial direction A. Usually, the desired axis of rotation defining the axial direction A corresponds to the central axis of the stator 6.

Within the framework of this application, a radial direction refers to a direction, which stands perpendicular on the axial direction A.

The rotor 3 comprises the magnetically effective core 31, which is designed here in a ring-shaped manner. The magnetically effective core 31 defines a magnetic center plane. The magnetic center plane of the magnetically effective core 31 of the rotor 3 refers to that plane perpendicular to the axial direction A in which the magnetically effective core 31 of the rotor 3 is levitated in the operating state when the rotor 3 is not tilted and not deflected in the axial direction A. As a rule, in a disk-shaped or ring-shaped magnetically effective core 31, the magnetic center plane is the geometric center plane of the magnetically effective core 31 of the rotor 3, which is perpendicular to the axial direction A. That plane in which the magnetically effective core 31 of the rotor 3 is levitated between the end faces 611 in the stator 6 in the operating state is also referred to as the radial plane. The radial plane defines the x-y plane of a Cartesian coordinate system whose z-axis extends in the axial direction A. If the magnetically effective core 31 of the rotor 3 is not tilted and not deflected with respect to the axial direction A, the radial plane coincides with the magnetic center plane.

The radial position of the magnetically effective core 31 or the rotor 3 refers to the position of the rotor 3 in the radial plane.

In FIG. 6, only the magnetically effective core 31 is represented from the rotor 3. It is understood that the rotor 3 can, of course, comprise other components such as a sheath 32 (FIG. 5) or an encapsulation 32, which are preferably made of a plastic, or of a metal, or of a metal alloy, or of a ceramic or a ceramic material.

As can be seen in particular in FIG. 5, the rotor 3 is designed as a whole in the form of a circular-cylindrical ring-disk, preferably with a central opening 33 which extends completely through the rotor 3 in the axial direction A, so that the fluid can also flow through this central opening 33.

The rotor 3 and in particular the magnetically effective core 31 of the rotor 3 are surrounded by the radially outwardly arranged transverse legs 613 of the coil cores 61 of the stator 6, so that the magnetically effective core 31 is surrounded by the end faces 611 facing it. The longitudinal legs 612 of the coil cores 61 each extend in the axial direction A from a first end, which is the lower end according to the representation (FIG. 6), to a second end, which is the upper end according to the representation. The transverse legs 613 are arranged at the upper ends of the longitudinal legs 612. Each transverse leg 613 extends in the radial direction towards the rotor 3.

When the magnetically effective core 31 of the rotor 3 is in its desired position during operation, the magnetically effective core 31 is centered between the end faces 611 of the transverse legs 613 so that the transverse legs 613 are arranged in the magnetic center plane and in the radial plane, respectively (in this case, these two planes are the same). According to the representation, the concentrated windings 62, 63 are arranged below the radial plane and are aligned such that their coil axes extend in the axial direction A.

All first ends of the longitudinal legs 612—i.e., the lower ends according to the representation (FIG. 6)—are connected to each other by a return 64. The return 64 is preferably designed in a ring-shaped manner. Such embodiments are possible (see FIG. 6) in which the return 64 extends radially inwardly along all first ends of the longitudinal legs 612. However, it is also possible that the return 64 has a plurality of recesses along its circumference, each of which receives one of the first ends. In the case of other embodiments, the return can also comprise a plurality of ring segments, each of which is arranged in each case between two circumferentially adjacent coil cores 61 in the region of the first ends. According to other embodiments, it is further possible to position the ring-shaped return 64 on the first ends of the longitudinal legs 612 in such a way that all of the first ends of the longitudinal legs 612 are arranged on the return 64. In this case, the longitudinal legs 612 and the ring-shaped return 64 are preferably designed with the same thickness in the radial direction. Then, the return 64 preferably consists of wound sheet metal (toroidal core) or of a powder-magnetic material (also called soft magnetic composites (SMC)).

In order to generate the electromagnetic rotating fields required for the magnetic drive and the magnetic levitation of the rotor 3, the longitudinal legs 612 of the coil cores 61 carry the windings designed as concentrated windings, namely the drive coils 62 and the control coils 63, wherein exactly one drive coil 62 and exactly one control coil 63 are arranged around each longitudinal leg 612 in the first embodiment. In the operating state, those electromagnetic rotating fields are generated with these concentrated windings 62, 63, with which a torque is effected on the rotor 3 and with which any adjustable transverse force can be exerted on the rotor 3 in the radial direction, so that the radial position of the rotor 3, i.e. its position in the radial plane perpendicular to the axial direction A, can be actively controlled or regulated.

The "magnetically effective core 31" of the rotor 3 refers to that region of the rotor 3 which magnetically interacts with the stator 6 for torque generation and the generation of the magnetic levitation forces.

Both the ring-shaped return 64 and the coil cores 61 of the stator 6 are each made of a soft magnetic material because they serve to guide the magnetic flux.

Suitable soft magnetic materials for the coil cores 61 and the return 64 are, for example, ferromagnetic or ferrimagnetic materials, i.e., in particular iron, nickel-iron, cobalt-iron, silicon iron or Mu-metal. In this case, for the stator 6, a design as a stator sheet stack is preferred, in which the coil cores 61 and the return 64 are designed in sheet metal, i.e., they consist of several thin sheet metal elements, which are stacked.

Furthermore, it is possible that the coil cores 61 and the return 64 consist of pressed and subsequently sintered grains of the aforementioned materials. The metallic grains are preferably embedded in a plastic matrix so that they are at least partially insulated from each other, whereby eddy current losses can be minimized. Thus, soft magnetic composites which consist of electrically insulated and compressed metal particles are also suitable for the stator. In particular, these soft magnetic composites, also designated as SMC (Soft Magnetic Composites), can consist of iron powder particles coated with an electrically insulating layer. These SMCs are then formed into the desired shape by powder metallurgy processes.

During operation of the electromagnetic rotary drive 90, the magnetically effective core 31 of the rotor 3 interacts with the stator 6 according to the principle of the bearingless motor also described in EP 1 284 415, in which the rotor 3 can be magnetically driven without contact and can be magnetically levitated without contact with respect to the stator 6. For this purpose, the stator 6 is designed as a bearing and drive stator, with which the rotor 3 can be magnetically driven without contact in the operating state about the desired axis of rotation—i.e., it can be set into rotation—and can be magnetically levitated without contact with respect to the stator 6. Three degrees of freedom of the rotor 3 can be actively regulated, namely its position in the radial plane and its rotation. With respect to its axial deflection from the radial plane in the axial direction A, the magnetically effective core 31 of the rotor 3 is passively magnetically stabilized by reluctance forces, i.e., it cannot be actuated. Also, with respect to the remaining two degrees of freedom, namely tilts with respect to the radial plane perpendicular to the desired axis of rotation, the magnetically effective core 31 of the rotor 3 is also passively magnetically stabilized. Due to the interaction of the magnetically effective core 31 with the coil cores 61, the rotor 3 is thus passively magnetically levitated or passively magnetically stabilized in the axial direction A and against tilts (a total of three degrees of freedom) and actively magnetically levitated in the radial plane (two degrees of freedom).

As is generally the case, an active magnetic levitation is also referred to in the framework of this application as one which can be actively controlled or regulated, for example by the electromagnetic rotating fields generated by the drive coils 62 and control coils 63. A passive magnetic levitation or a passive magnetic stabilization is one that cannot be controlled or regulated. The passive magnetic levitation or stabilization is based, for example, on reluctance forces, which bring the rotor 3 back again to its desired position when it is deflected from its desired position, e.g., when it is displaced or deflected in the axial direction A or when it is tilted.

A radial levitation or a levitation in a radial manner refers to a levitation of the rotor 3 with which the radial position of the rotor 3 can be stabilized, i.e., a levitation which levitates the rotor 3 in the radial plane and thus with respect to its radial position.

An axial levitation or a levitation in an axial manner and an axial stabilization or a stabilization in an axial manner, respectively, refers to a levitation or a stabilization of the rotor 3 with which, on the one hand, the position of the rotor 3 is stabilized with respect to the axial direction A and with which, on the other hand, the rotor 3 is stabilized against tilts. Such tilts represent two degrees of freedom and designate deflections in which the momentary axis of rotation of the rotor 3 no longer points exactly in the axial direction A but encloses an angle different from zero with the desired axis of rotation. In the case of a tilt, the magnetic center plane thus no longer lies in or parallel to the radial plane, but the magnetic center plane encloses an angle with the radial plane E that is different from zero.

According to the principle of the bearingless motor, in contrast to classical magnetic bearings, the magnetic levitation and the drive of the motor is realized by electromagnetic rotating fields. Typically, in the bearingless motor, the magnetic drive and levitation function is generated by the superposition of two magnetic rotating fields, which are usually designated as the drive and control fields. These two rotating fields generated with the drive coils 62 and the control coils 63 of the stator 6 usually have a pole pair number that differs by one. For example, if the drive field has the pole pair number p, the control field has the pole pair number p+1 or p−1. In this case, tangential forces acting on the magnetically effective core 31 in the radial plane are generated by the drive field, causing a torque, which causes the rotation about the axial direction A. Due to the superposition of the drive field and the control field, it is also possible to generate a transverse force on the magnetically effective core 31 in the radial plane which can be adjusted as desired, with which the position of the magnetically effective core 31 in the radial plane can be regulated. Thus, it is not possible to divide the electromagnetic flux generated by the coils 62, 63 into an (electro-) magnetic flux that only provides for driving the rotation and an (electro-) magnetic flux that only realizes the magnetic levitation.

Figure 11:
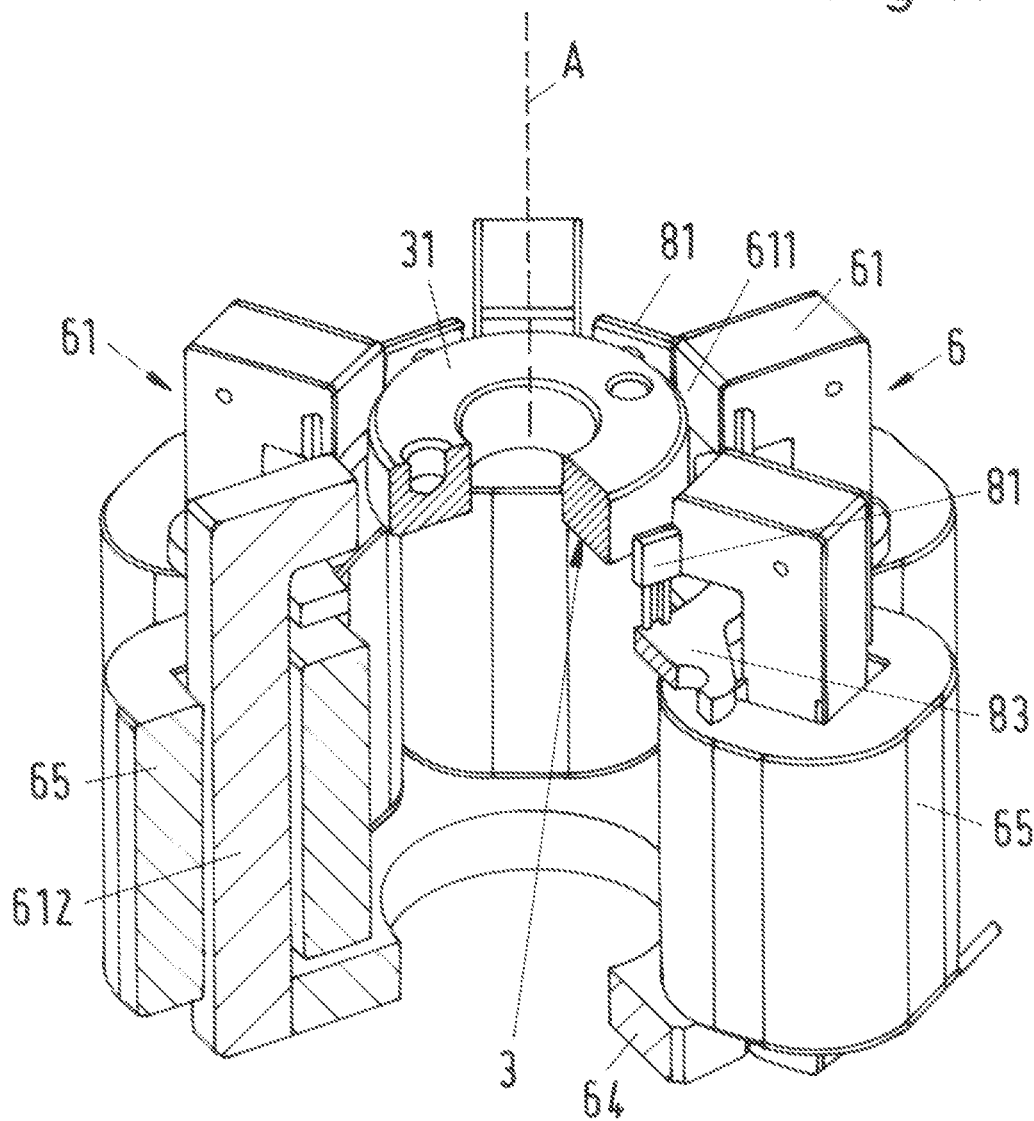
FIG. 11 is as FIG. 6, but for a second embodiment of a viscometer according to the invention.

To generate the drive field and the control field, it is possible on the one hand—as shown in FIG. 6—to use two different winding systems, namely the drive coils 62 to generate the drive field and the control coils 63 to generate the control field. The current impressed in these coils is then designated as the drive current or the control current. On the other hand, it is also possible (see the second embodiment, which is represented in FIG. 11) to generate the drive and levitation function with only one single winding system, so that there is therefore no distinction between drive coils 62 and control coils 63. This can be realized in such a way that the values for the drive current and the control current determined in each case by the control device 8 are added or superimposed by calculation—e.g., with the aid of software—and the resulting total current is impressed into the respective concentrated winding 65 (FIG. 11). In this case, of course, it is no longer possible to distinguish between control coils and drive coils.

In the first embodiment described here, two separate winding systems are provided in the stator 6, namely one with the separate drive coils 62 and one with the separate control coils 63.

The viscometer according to an embodiment of the invention is based on the principle of rotating the rotor in the measuring chamber 23 and thus in the fluid and determining the viscosity from the electrical drive power which is required to drive the rotation of the rotor 3 in the fluid at a known rotational speed.

The magnetic drive field, which is generated by the drive coils 62 is an electromagnetic rotating field which exerts a torque on the magnetically effective core 31 of the rotor 3, thereby causing the rotor 3 to rotate. The drive field can be controlled by a drive current according to the well-known method of field-oriented control (vector control). Within the framework of this application, the term "drive current" designates the current that must be fed into the stator 6 of the electromagnetic rotary drive 90 to generate the torque that drives the rotation of the rotor 3.

If no or only a negligibly small hydraulic power (pumping power) is provided by the rotor 3 during operation, the drive current required for torque generation is only dependent on the internal friction and thus on the viscosity of the fluid. Thus, the viscosity of the fluid can be determined from the electrical drive current required to generate the torque that drives the rotation of the rotor 3 and the rotational speed (rotational frequency) of the rotor 3.

In the following, it is assumed that the rotor 3 provides at most a negligibly small hydraulic power (pumping power). If the hydraulic power should not be negligibly small, the hydraulic power can be determined by measurement in a simple manner and then subtracted, so that only the drive power required for the rotation of the rotor remains.

Within the framework of this application, it is referred to the electric current as a possible operating parameter of the electromagnetic rotary drive. However, it is understood that the electric current is to be understood only as an example of an operating parameter or electrical operating parameter. The explanations also apply in the analogously same way to other operating parameters such as the rotational speed at which the rotor 3 rotates, or to other electrical operating parameters such as, for example, the electrical voltage or the electrical power.

In the operating state, the fluid thus flows through the measuring device 10. Here, the largest part of the fluid flows as a main flow through the main flow connection 26, while a smaller secondary flow flows around the rotor 3 or through the central opening 33. The rotor 3 is driven for rotation at a constant and predeterminable rotation speed or rotational speed. The drive current required for this rotation speed or rotational speed is determined, and the viscosity of the fluid is then determined from this—for example in the control device 8.

Furthermore, it is also possible to apply the drive device 50 or the stator 6 of the electromagnetic drive 90 with a constant, adjustable or predeterminable drive current, which generates a constant torque. Depending on the viscosity of the fluid, a rotational speed is then established which can be used to determine the viscosity. In the case of a given drive current or torque, there is an inversely proportional relationship between the rotational speed and the viscosity, i.e., a lower viscosity results in a higher rotational speed or rotation speed of the rotor 3 and a higher viscosity in a lower rotational speed. These relationships can be stored for different drive currents as a three-dimensional characteristic field in the control device 8 or can be represented at least approximately by algebraic formulas. During operation, the drive current is then selected such that the expected viscosity range can be covered by the rotational speed range of the drive device 50.

According to a preferred measure, the drive device 50 comprises at least one magnetic field sensor (FIG. 6) with which the rotor magnetic field HR can be determined. In the first embodiment, several magnetic field sensors are provided, namely a plurality of radial magnetic field sensors 81, each of which is arranged such that it can measure at its location the radial component of the rotor magnetic field (HR), and at least one axial magnetic field sensor 82 which is arranged such that it can measure at its location the axial component of the rotor magnetic field HR. Preferably, each magnetic field sensor 81, 82 is designed as a Hall sensor, but of course all other types of magnetic field sensors are also suitable for the viscometer 1 according to embodiments of the invention.

As FIG. 6 in particular shows, one of the radial magnetic field sensors 81 is arranged in each case between two circumferentially adjacent transverse legs 613, so that a total of six radial magnetic field sensors 81 are provided here. With respect to the axial direction A, all radial magnetic field sensors 81 are arranged at the same height as the magnetically effective core 31 of the rotor 3, so that all radial magnetic field sensors 81 are opposite to the magnetically effective core 31 and face it.

Preferably, all radial magnetic field sensors 81 are arranged on a sensor circuit board or a sensor PCB (PCB printed circuit board) 83. The sensor PCB 83 is preferably designed substantially ring-shaped and arranged below the transverse legs 613 with respect to the axial direction A, namely in the space between the control coils 63 and the transverse legs 613. Furthermore, at least one axial magnetic field sensor 82 is preferably provided on the sensor PCB, which is arranged and oriented such that it can be used to determine the axial component of the rotor magnetic field HR at its location.

Other sensors can also be provided on the sensor PCB 83, such as position sensors for determining the position of the rotor 3 in the radial plane or other sensors which are necessary or advantageous for the operation of the electromagnetic rotary drive 90. The sensor PCB 83 is signal-connected to the control device 8 so that the measured values determined with the magnetic field sensors 81, 82 can be transmitted to the control device 8.

The determination of the viscosity can be further improved by the magnetic field sensors 81, 82 because changes in the rotor magnetic field HR can be detected and then also compensated for, so that falsifications of the viscosity determination can be avoided.

Such changes in the rotor magnetic field HR can be caused, for example, by temperature changes of the permanent magnet in the magnetically effective core 31 of the rotor 3. Thus, for example, it is possible that the fluid flowing through the measuring device 10 heats up the magnetically effective core 31 of the rotor 3 so that its temperature increases. Due to this temperature increase, the rotor magnetic field HR then reduces. Such changes in the rotor magnetic field HR can be detected with high accuracy and great reliability in particular with the radial magnetic field sensors 81.

Another cause of changes in the rotor magnetic field HR can be the asymmetry of the hydraulic flow at the rotor 3. The upper side of the rotor 3 is overflowed much more, namely by the main flow in the main flow connection 26 than other areas of the rotor 3. For example, the surface of the rotor 3 facing the bottom 24 is subjected to a much lower flow. If, for example, there are now changes in the total flow of the fluid through the measuring device 10, the main flow above the rotor 3 changes particularly noticeably as a result. This can lead to the fact that the position of the rotor 3 changes with respect to the axial direction A. Due to the change in hydraulic flow around the rotor 3, the rotor 3 can be lifted, i.e., moving away from the bottom 24, or the rotor 3 can be lowered, i.e., moving closer to the bottom 24. Such changes in the axial position of the rotor 3 lead to changes in the rotor magnetic field HR. Such changes can be detected particularly well with the axial magnetic field sensor 82 and then compensated for in the control device 8 when determining the viscosity.

If—as shown in FIG. 6—several radial magnetic field sensors 81 and at least one axial magnetic field sensor 82 are provided, it is also possible to determine the axial magnetic field sensor 82 only for the determination of the sign of the axial displacement, i.e., whether the rotor 3 is displaced upward or downward with respect to the axial direction A. The amplitude of the axial displacement, i.e., the amount by which the rotor 3 is displaced with respect to the axial direction A, can be determined from the signals of the radial magnetic field sensors 81. Determining the amplitude of the axial displacement with the help of the radial magnetic field sensors 81 has the advantage that, in particular in the case of several symmetrically or pairwise symmetrically arranged radial magnetic field sensors 81, the influence of tilting of the rotor or the influence of other field disturbances of the rotor magnetic field HR, e.g. by magnetic interference fields, is compensated, whereby the accuracy of the determination of the axial position of the rotor 3 is increased.

Preferably, the measuring device 10 comprises all components that come into contact with the fluid during the measurement process, while the components of the drive device 50 do not come into contact with the fluid. Thus, for example, it is possible to separate the measuring device 10 from the drive device 50 at the end of a process, to clean and/or sterilize it, and then reinsert it into the drive device 50 so that the viscometer 1 is ready for a new measurement or for a new process. This enables a particularly easy handling of the viscometer.

According to a particularly preferred embodiment, the measuring device 10 is designed as a single-use device for single use, and the drive device 50 is designed as a reusable device for multiple use or for continuous use.

The term "single-use device" and other combinations with the component "single-use", such as single-use part, single-use component, etc., refer to those components or parts which are designed for single-use, i.e., which can be used only once as intended and are then disposed of. For a new application, a new, previously unused single-use part must then be inserted. When configuring or designing the measuring device 10 as a single-use device, substantial aspects are therefore that the single-use device can be produced as simply and economically as possible, generate few costs and can be produced from materials, for example plastics, that are available at the lowest possible price. It is another substantial aspect that the single-use device, i.e., in this case the measuring device 10, can be assembled as easily as possible with the reusable device, i.e., in this case the drive device, to form the viscometer 1. The single-use device should therefore be able to be replaced very easily without the need for high assembly effort. Particularly preferred, the single-use device should be able to be assembled with or separated from the reusable device without the use of tools.

It is also an important aspect that the single-use device can be disposed of as easily as possible after use. For this reason, preference is given to materials that cause the least possible environmental impact, in particular also during disposal.

Furthermore, when the measuring device 10 is designed as a single-use device, it is particularly preferred that the parts made of plastic, i.e., for example the measuring housing 20 or the sheath 32, are made of a plastic that is as inexpensive as possible and commercially available. It is a further substantial aspect that the measuring device 10, which is designed as a single-use device, or its components must be sterilizable for certain fields of application. It is particularly advantageous if the measuring device 10, which is designed as a single-use device, can be gamma-sterilized. In this type of sterilization, the element to be sterilized is exposed to gamma radiation. The advantage of gamma sterilization, for example in comparison to steam sterilization, is in particular that sterilization can also take place through the packaging. Particularly in the case of single-use parts, it is common practice that the parts are placed in the packaging after production and then stored for some time before being delivered to the customer. In such cases, sterilization takes place through the packaging, which is not possible with steam sterilization or other methods.

A further advantage of gamma sterilization compared to steam sterilization is that gamma sterilization does not have to be performed at a high or elevated temperature. Steam sterilization, on the other hand, must be performed at a high temperature. Due to this high temperature, there is the risk that plastic components of the single-use device in particular can be destroyed or damaged. For example, plastic components can warp, whereby important or critical dimensions of the components, for example the outer diameter of the rotor 3 can be changed.

The measuring device 10, which is designed as a single-use device, has the great advantage that, because it can be used only once, it is not necessary to attach importance to good cleanability of the single-use device in the design, because the single-use device does not have to be cleaned when used as intended. Furthermore, it is usually not necessary that the single-use device or its components have to be sterilizable more than once. In particular for gamma sterilization, this is a great advantage, because the application of gamma radiation can lead to degradation of plastics, so that multiple gamma sterilization can make the plastic unusable.

Since sterilization under high temperatures and/or under high (steam) pressure can usually be dispensed with for single-use parts, more cost-effective plastics can be used, for example those which cannot withstand high temperatures, or which cannot be subjected to high temperature and pressure values several times.

Taking all these aspects into account, it is therefore preferred to use such plastics and such components for the production of the measuring device 10 as a single-use device that can be gamma-sterilized at least once. The materials and the components should be gamma-stable for a dose of at least 40 kGy to allow a single gamma sterilization. In addition, no toxic substances should be produced during gamma sterilization. In addition, it is preferred that all materials that come into contact with the fluid meet USP Class VI standards. Furthermore, it is preferred that all materials that come into contact with the fluid are free of components of animal origin (animal free) to prevent contamination of the fluid with prions. Prions could lead to dangerous diseases such as BSE or TSE.

For the production of the parts of the measuring device 10 that consist of plastic, the following plastics are preferred, for example polyethylene (PE), polypropylene (PP), low-density polyethylene (LDPE), ultra-low-density polyethylene (ULDPE), high density polyethylene (HDPE), ethylene-vinyl acetate (EVA), polyethylene terephthalate (PET), polyvinyl chloride (PVC), polyvinylidene fluoride (PVDF), acrylonitrile butadiene styrene (ABS), polyacrylic, polycarbonate (PC).

Less suitable or even unsuitable materials for manufacturing the plastic parts of the measuring device 10 are, for example, the materials polytetrafluoroethylene (PTFE) and perfluoroalkoxy polymers (PFA), which are known under the brand name Teflon. In the case of these materials, there is the risk of hazardous gases escaping during gamma sterilization, such as fluorine, which can then form toxic or harmful compounds such as hydrofluoric acid (HF).

With regard to applications in biotechnology, it is preferred that at least the components that come into contact with the fluid consist of a biocompatible material.

On the basis of FIG. 1 to FIG. 3, the simple assembly of the measuring device 10 with the drive device 50 will now be explained. In the first embodiment, the measuring device 10 and the drive device 50 can be connected to and separated from each other via a bayonet connection. For this purpose, the measuring housing 20 comprises a plurality of sector-shaped projections 4, here three, which are arranged along the circumference of the measuring housing 20. In the upper edge region of the drive housing 60, a plurality of recesses 7 are arranged along the inner circumference of the drive housing 60, the number of recesses 7 corresponding to the number of projections 4. The recesses 7 are dimensioned and arranged with respect to the circumferential direction in such a way that in each case one of the projections 4 can be inserted into one of the recesses 7 in the axial direction A. A lug 71 is arranged in each case between two circumferentially adjacent recesses, which projects beyond the recesses 7 when viewed inward in the radial direction. Each lug 71 is designed in such a way that it can engage over one of the projections 4. Furthermore, a securing pin 51, for example spring-loaded, is provided in the upper edge region of the drive housing 60, which can be pulled outwards in the radial direction. A securing opening 41 is disposed on the measuring housing 20, which is designed and arranged in such a way that the securing pin 51 engages in the securing opening 41 if the measuring device 10 is fixed to the drive device 50.

To establish and fix the connection of the measuring device 10 with the drive device 50, the securing pin 51 is pulled outwards in the radial direction, as shown by the arrow C in FIG. 1. The measuring device 10 is inserted into the drive device 50 in the axial direction A so that each of the recesses 7 receives in each case one of the projections 4. This is indicated by the arrow B in FIG. 1. FIG. 2 shows the condition in which the projections 4 are fully inserted into the recesses 7. Now the measuring device 10 is rotated by a fraction of a rotation about the axial direction A (see arrow D in FIG. 2) so that the projections 4 slide under the lugs 71. Subsequently, each projection 4 is engaged by one of the lugs 71 so that the measuring device 10 is fixed to the drive device 50. Finally, the securing pin 51 is moved radially inwards (see arrow E in FIG. 3) so that the securing pin 51 engages in the securing opening 41 and prevents a further rotation of the measuring device 10 relative to the drive device 50. If the securing pin 51 is designed in a spring-loaded way, it automatically engages the securing opening 41 as soon as it is in the correct position.

Figure 3:
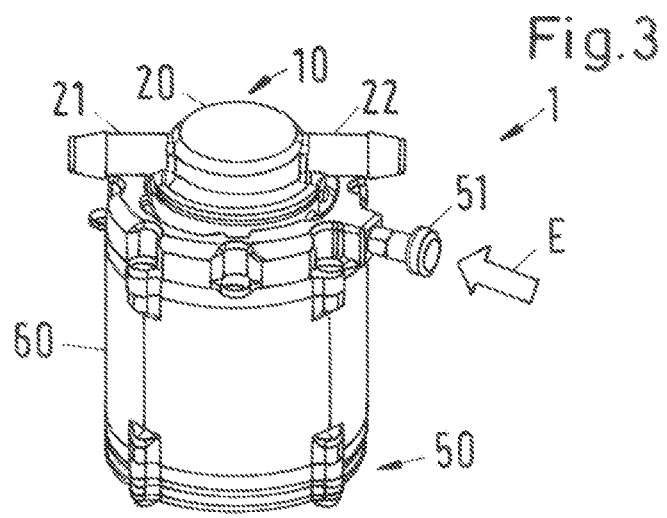
FIG. 3 illustrates as FIG. 1, but after assembling the viscometer.

FIG. 3 shows the viscometer in the assembled and operational state, with the measuring device 10 inserted into and fixed to the drive device 50. The separation of the measuring device 10 from the drive device 50 is carried out in the same way as the assembly.

It is understood that the projections 4 do not all have to be designed in the same way. For example, they can differ from each other by their length in the circumferential direction. This can be advantageous if the measuring device 10 is to be insertable into the drive device 50 in exactly one orientation only.

Figure 2:
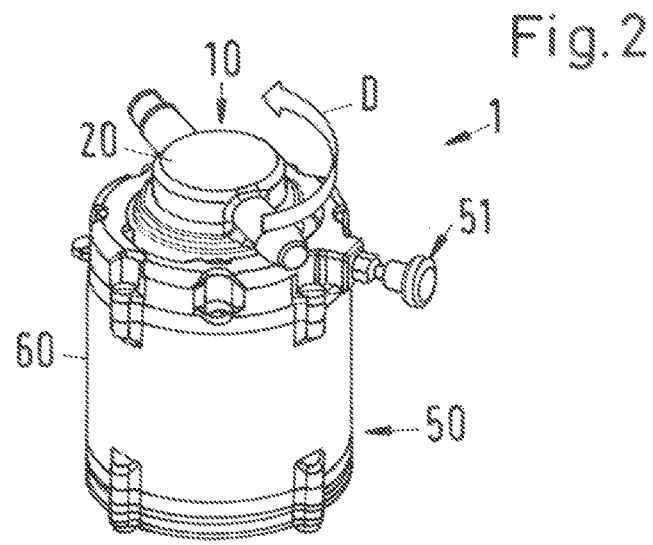
FIG. 2 illustrates as FIG. 1, but during assembly of the viscometer.
Figure 7:
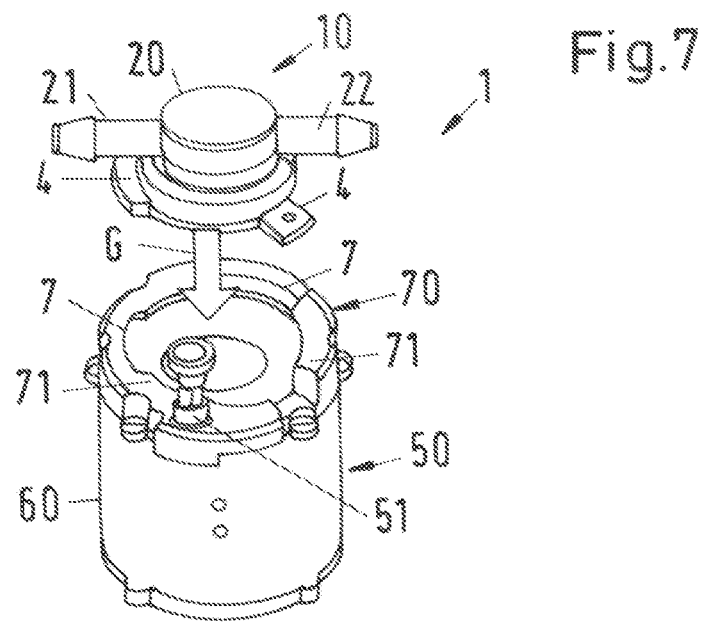
FIGS. 7-9 are as FIGS. 1-3, but for a first variant of the first embodiment.
Figure 8:
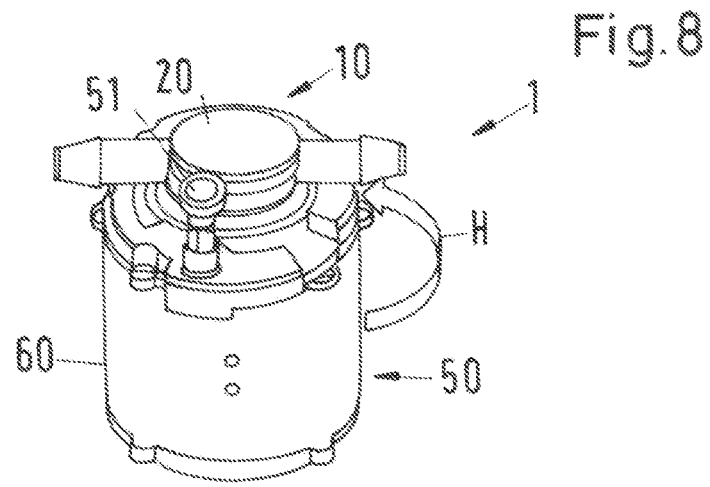
Figure 9:
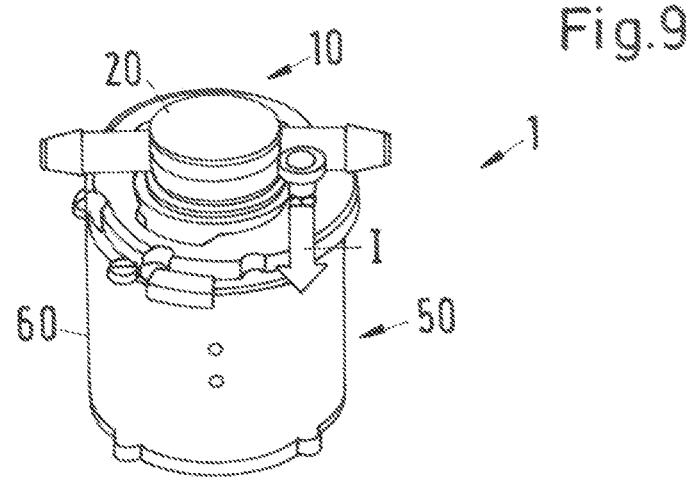

In FIG. 7 to FIG. 9, a first variant of the first embodiment example is represented in a representation corresponding to FIG. 1 to FIG. 3. This first variant differs only in the design of the connection between the measuring device 10 and the drive device 50. In the following, only the differences between the first variant and the first embodiment will be discussed. Otherwise, the previous explanations also apply in the analogously same way to the first variant.

In the first variant, the drive device 50 comprises a connecting means or device 70, which is designed in a ring-shaped manner and arranged at the upper edge region of the drive housing 60 in such a way that the connecting means 70 forms the upper edge region of the drive housing 60. The ring-shaped connecting means 70 is designed such that it is rotatable with respect to the drive housing 60 between an open position, which is represented in FIG. 7 and FIG. 8, and a closed position, which is represented in FIG. 9. The recesses 7 with the lugs 71 arranged therebetween are provided in or on the connecting means 70.

As can be seen in particular in FIG. 7, in the first variant, the projections 4—and accordingly also the recesses 7—are designed with different lengths in the circumferential direction, so that the measuring device 10 can only be inserted in the drive device 50 in exactly one position.

The measuring device 10 can be inserted into and separated from the drive device 50 only when the connecting means 70 is in the open position, which is represented in FIG. 7 and in FIG. 8. When the connecting means 70 is in the closed position, which is represented in FIG. 9, the lugs 71 provided on the connecting means 70 engage over the projections 4 so that the measuring housing 20 and the drive housing 60 are fixed relative to each other.

In the first variant, the securing pin 51 is designed such that it secures the connecting means 70 against a rotation relative to the drive housing 60 when the connecting means 70 is in the closed position. For this purpose, the securing pin 51 is designed movably in the axial direction A in the first variant. When the connecting means 70 is in the closed position, the securing pin 51 fixed to the connecting means 70 engages in a securing opening in the drive housing 60, so that the connecting means 70 is fixed in the closed position and can no longer be rotated relative to the drive housing 60 without first actuating the securing pin 51 in the axial direction A.

For assembly, the connecting means 70 is moved to the open position, which is shown in FIG. 7. The measuring device 10 is then inserted through the connecting means 70 into the drive device 50, as indicated by the arrow G in FIG. 7. In the process, the projections 4 are received by the recesses 7. When the measuring device 10 is inserted into the drive device (see FIG. 8), the connecting means 70 is rotated from the open position to the closed position by a rotation relative to the drive housing 60 and about the axial direction A, as indicated by the arrow H in FIG. 8. When the connecting means 70 is in the closed position represented in FIG. 9, the securing pin 51 is moved downward in the axial direction A according to the representation, as indicated by the arrow I in FIG. 9, so that the securing pin 51 engages in the securing opening in the drive housing 60 and prevents a further rotation of the connecting means 70 relative to the drive housing 60. If the securing pin 51 is designed in a spring-loaded way, it automatically engages in the securing opening as soon as the connecting means 70 is in the closed position.

The first variant represented in FIG. 7 to FIG. 9 is particularly advantageous if the viscometer 1 is integrated in a fluid system in which it is not possible to rotate the measuring device 10 relative to the drive device 50 when replacing the measuring device 10, for example because the inlet 21 and/or the outlet 22 must be connected to rigid, i.e., non-flexible, lines.

In other embodiments, it is also possible that the measuring device 10 and the drive device 50 can be detachably connected to each other by a click connection, a snap connection, or a snap-in connection.

Figure 10:
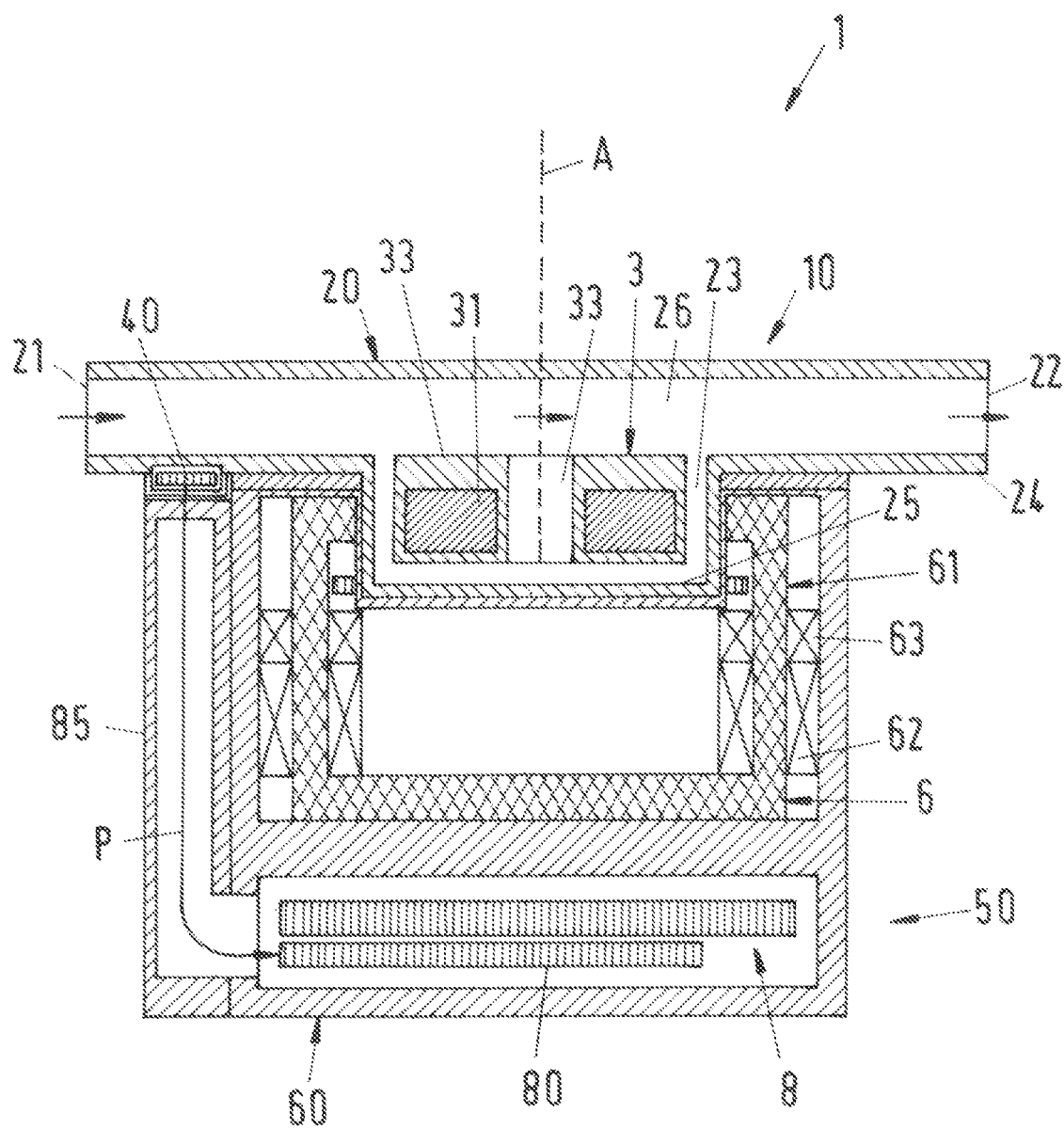
FIG. 10 is as FIG. 5, but for a second variant of the first embodiment.

FIG. 10 shows a second variant of the first embodiment in a representation analogous to FIG. 5. In the following, only the differences to the previously described embodiments will be discussed. It is understood that all the previous explanations also apply in the same way or in the analogously same way to the second variant.

In the second variant, the measuring device 10 comprises a storage unit 40 in which calibration data and optionally other identification data are stored, which are specific to this measuring device 10. The drive device 50 comprises an interface 85 via which data from the storage unit 40 can be transmitted to the control device 8. In particular for measurements that require a very high precision, it is often necessary that the viscometer 1 is calibrated. For this purpose, the measuring device 10 should then usually be calibrated together with the drive device 50. If the measuring device 10, which is designed as a single-use device, for example, is now replaced by a new measuring device 10, it might be necessary to recalibrate the viscometer 1, which now comprises this new measuring device 10—inserted in the original drive device 50. For example, minute variations in the geometric dimensions of components of the measuring device, such as minute variations in the outer diameter of the rotor 3 or in its magnetic properties, can result in the need for a new calibration after the measuring device has been replaced. Such variations are, for example, due to manufacturing technology and are usually unavoidable, at least not at a reasonable effort.

To solve this problem, for example, each measuring device 10 in a reference viscometer can be calibrated with a reference drive device. The resulting calibration data specific to the respective measuring device 10 is then stored in the storage unit 40 of this measuring device 10. If this measuring device 10 is now inserted into the drive device 50, the specific calibration data is transmitted to the control unit 8 of the drive device 50 via the interface 85, so that it is no longer necessary to recalibrate the viscometer 1 after replacing the measuring device 10.

The control unit 8 comprises a storage reader unit 80, which is also arranged in the drive housing 60 and which is signal-connected to the interface 85. Thus, the calibration data for the measuring device 10 stored in the storage unit 40 can be read out via the interface 85 and transmitted to the storage reading unit 80 of the control device 8. This data flow is represented in FIG. 10 by the arrow with the reference sign P.

Since the measuring device 10 is preferably designed to be gamma-sterilizable, the storage unit 40 is also preferably designed to be gamma-stable, i.e., the storage unit 40 is designed in such a way that it does not suffer any damage during gamma sterilization and, in particular, does not lose any calibration data. For example, suitable gamma-stable storage units 40 are: FRAM (Ferroelectric Random Access Memory), RFID elements (RFID: Radio Frequency Identification), or optoelectronically readable elements such as barcodes or two-dimensional codes, e.g. QR codes (QR: Quick Response).

In a representation analogous to FIG. 6, FIG. 11 shows a second embodiment of a viscometer 1 according to the invention, which differs from the first embodiment in the design of the electromagnetic rotary drive 90. In the following, only the differences to the first embodiments will be discussed. The same parts or functionally equivalent parts of the second embodiment are designated with the same reference signs as in the first embodiment or its variants. In particular, the reference signs have the same meaning as already explained in connection with the first embodiment and its variants. It is understood that all previous explanations of the first embodiment and its variants also apply in the same way or in the analogously same way to the second embodiment.

In the second embodiment, the electromagnetic rotary drive 90 is designed with only one winding system comprising six concentrated windings 65. Exactly one concentrated winding 65 is arranged on the longitudinal leg 612 of each coil core 61. In the second embodiment, the drive and bearing function is realized with only one single winding system, namely the six concentrated windings 65, so that there are no separate drive and control coils as in the first embodiment. In the process, the drive and bearing function can be realized such that the respective values determined by the control device 8 for the drive and control currents are added or superimposed by calculation—e.g., with the aid of software—and the resulting total current is impressed in the respective concentrated winding 65.

In the following, some more embodiments of components are now described, which can be used for both the first embodiment and the second embodiment.

Figure 12:
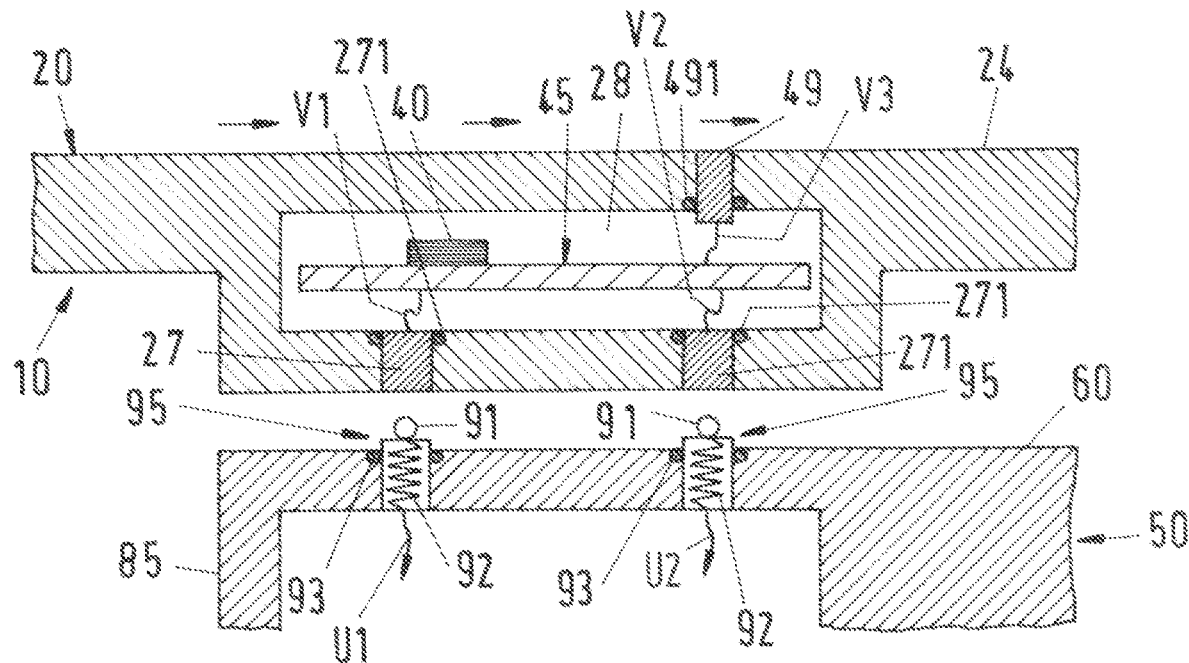
FIG. 12 illustrates a possible embodiment for a signal connection enabling an electrical connection between the measuring device and the drive device.

FIG. 12 shows a possible embodiment for a signal connection between the measuring device 10 and the drive device 50, for example to transfer calibration data from the storage unit 40 of the measuring device 10 to the control device 8 of the drive device 50. The signal connection represented in FIG. 12 is designed as an electrical signal connection. The signal connection is preferably designed in such a way that it can easily withstand a multiple replacement of the measuring device 10.

In that surface of the drive housing 60 of the drive device 50 which faces the measuring device 10 in the assembled state, i.e., when the measuring device 10 is inserted into the drive device 50, one or more spring contacts 95 are provided, each of which comprises a conductive head 91 projecting from the surface of the drive housing 60, which is spring-loaded by a spring element 92. In the embodiment represented in FIG. 12, two such spring contacts 95 are represented with an exemplary character. It is understood that in other embodiments, only one spring contact 95 or more than two spring contacts 95 can be provided. Each of the spring contacts 95 is signal-connected to the control device 8, for example to the storage reading unit 80 of the control device 8, by an electrical signal connection U1 or U2. The head 91 of the spring contacts 95 is preferably made of gold.

Electrical contacts 27 are disposed in the bottom 24 of the measuring housing 20 of the measuring device 10, which contacts are arranged such that they press on the spring contacts 95 in the assembled state, i.e., when the measuring device 10 is inserted into the drive device 50 and thus form an electrical connection between the measuring device 10 and the drive device 50.

The electrical contacts 27 are each protected by a sealing element 271, for example an O-ring, against the escape of fluid from the measuring device 10. It is also possible to attach the electrical contacts 27 to the measuring housing 20 in a sealing manner by a glued connection, or to overmold the electrical contacts 27 with the plastic during the manufacture of the measuring device 10, which is preferably performed using an injection molding process.

The spring contacts 95 are each protected by a sealing element 93, for example as an O-ring, against the penetration of the fluid into the drive device 50. The fluid is also represented in FIG. 12 by the arrows without reference signs.

According to the representation, a cavity 28 is disposed in the bottom 24 of the measuring device 10 above the electrical contacts 27, which cavity is designed as a closed hollow space. A storage PCB 45 is disposed in the cavity 28 on which the storage unit 40 is arranged. The storage PCB 45 is connected to the electrical contacts 27 in the bottom 24 of the measuring housing 20 via electrical signal connections V1, V2. The electrical signal connections V1 and V2 can also be designed as a direct physical contact between the storage PCB 45 and the electrical contacts 27.

The electrical signal connections U1, U2 in the drive device 50 and the electrical signal connections V1 and V2 can each be in the form of a wire.

The storage PCB 45 can be designed to be able to communicate and/or to provide electrical power. For example, the storage PCB 45 can be designed as part of a bus system, such as for an SPI (Serial Peripheral Interface) or for an I²C bus (I2C: Inter-Integrated Circuit).

Optionally, but preferably, the measuring device 10 comprises a temperature sensor 49 with which the temperature of the fluid in the measuring device 10 can be determined. Since the viscosity of very many fluids has a distinct temperature dependence, it is advantageous to determine the temperature of the fluid as close as possible to the location where the viscosity of the fluid is also determined.

As is represented in FIG. 12, the temperature sensor 49 can be arranged in the cavity 28 in such a way that it extends completely through the wall which delimits the cavity 28 and which is overflowed by the fluid in the operating state. Thus, the temperature sensor 49 is in direct physical contact with the fluid in the operating state, which enables a particularly accurate determination of the temperature of the fluid.

On the other hand, since the temperature sensor 49 is arranged in or on the cavity 28, it can be connected to the storage PCB 45 via an electrical signal connection V3 so that the storage PCB 45 can supply power to the temperature sensor 49 and receive measurement signals from the temperature sensor 49.

The temperature sensor 49 can be fixed in the bottom 24 of the measuring device 10 in various ways. For example, it can be fixed in a hole provided for this purpose by gluing or by a press-fit. It is also possible to overmold the temperature sensor 49 with the plastic during the manufacture of the measuring device 10, which is preferably performed using an injection molding process. Depending on the attachment of the temperature sensor 59 in the bottom 24 of the measuring device 20, it can be advantageous to provide a sealing element 491, such as an O-ring, on the temperature sensor 49 to prevent a penetration of the fluid into the cavity 28.

Of course, it is also possible to arrange the temperature sensor 49 at other positions of the measuring device 10 or the measuring housing 20, for example at or in an upper part 101 (FIG. 23) or at the inlet 21 or at the outlet 22. Depending on the design, it can be advantageous to connect the temperature sensor 49 directly to the control device 8 via a separate signal line.

Another possibility is to design the measuring device 10 such that it can be brought into thermal contact with an external temperature sensor to determine the temperature of the fluid, wherein the external temperature sensor is not a component of the measuring device 10. For example, this can be realized such that a metallic contact surface, e.g., a metal sleeve, is provided at the inlet 21 or at the outlet 22, which, on the one hand is in thermal contact with the fluid flowing through the measuring device 10 and which, on the other hand can be brought into thermal contact with an external temperature sensor. The external temperature sensor is signal-connected to the control device 8. The metallic contact surface or the metal sleeve can, for example, be arranged in a recess at the inlet 21 or preferably at the outlet 22, into which the external temperature sensor can be inserted, or in which the external temperature sensor can be fixed in another way.

In principle, all temperature sensors 49 known per se are suitable for the viscometer 1. With regard to the highest possible flexibility with respect to the fluid, the temperature sensor 49 is preferably designed to be corrosion-resistant. Furthermore, a metallic temperature sensor 49 is preferred.

As an alternative or in addition, a temperature sensor 59 can also be provided in the drive device 50 for capturing the temperature of the fluid in the measuring device 10. In a detailed representation, FIG. 13 and FIG. 14 each show such an arrangement of the temperature sensor 59 in the drive device 50. With respect to the selection and attachment of the temperature sensor 59, the same applies analogously as explained above for the temperature sensor 49 in the measuring device 10.

The temperature sensor 59 provided in the drive device 50 is also arranged such that, in the operating state, it is as close as possible to the fluid flowing through the measuring device 10 and can come into thermal contact with the fluid.

Figure 13:
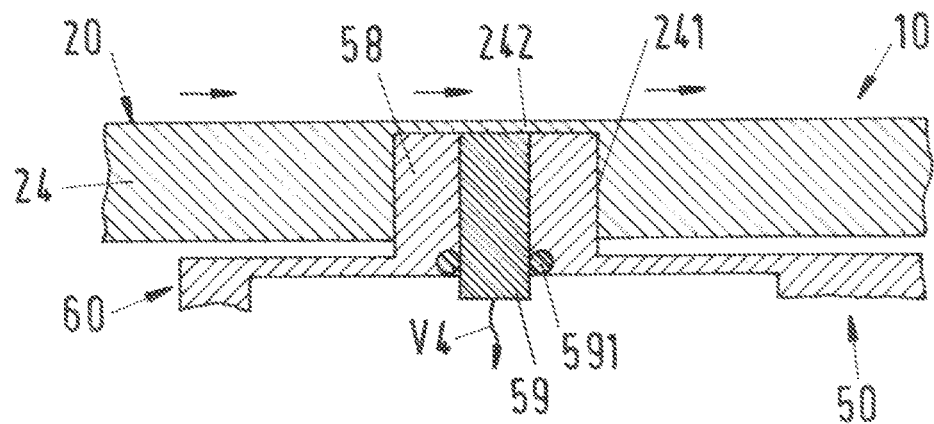
FIG. 13 illustrates a detailed representation to illustrate the arrangement of a temperature sensor.
Figure 14:
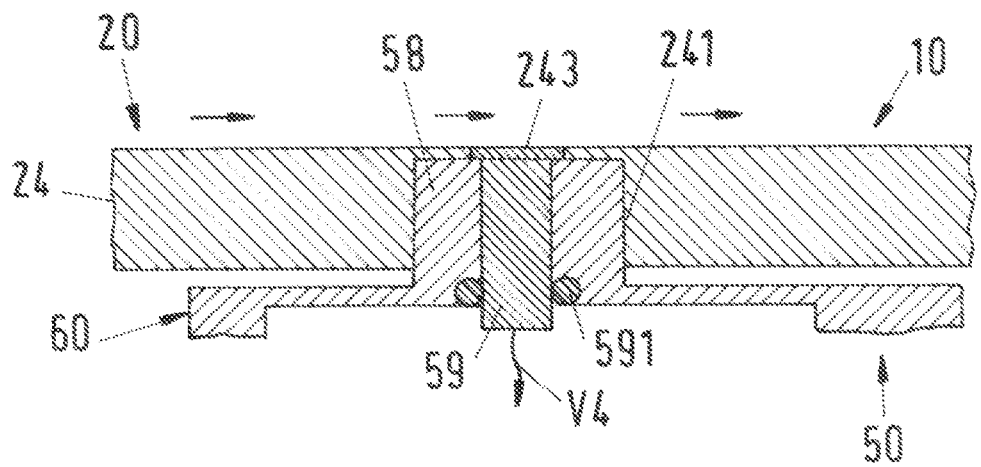
FIG. 14 is as FIG. 13, but for another embodiment.

In the arrangements represented in FIG. 13 and FIG. 14, the temperature sensor 59 is in each case placed in that wall of the drive housing 60 which, in the assembled state, i.e., when the measuring device 10 is inserted into the drive device 50, faces the measuring housing 10 or adjoins or abuts the measuring housing 10. A receptacle 58 for the temperature sensor 59 is disposed in this wall of the drive housing 60. The receptacle 58 is designed in such a way that it protrudes from the wall. The temperature sensor 59 is connected to the control device 8 via an electrical signal connection V4.

Depending on the attachment of the temperature sensor 59 in the receptacle 58, it can be advantageous to provide a sealing element 591, such as an O-ring, on the temperature sensor 59 to prevent a penetration of the fluid into the drive device 50. It is also possible to attach the temperature sensor 59 to the drive housing 60 in a sealing manner by a press-fit or glued connection, or to overmold the temperature sensor 59 with the plastic during the manufacture of the drive housing 60, which is preferably performed using an injection molding process.

A hole 241 is disposed in the bottom 24 of the measuring device 10, which hole 241 is designed and arranged in such a way that the receptacle 58 engages the hole 241 in a custom-fit manner when the measuring device 10 is inserted into the drive device 50.

In the embodiment represented in FIG. 13, the hole 241 is designed such that it does not completely penetrate the bottom 24 of the measuring housing 20, but that a thin region of the bottom 24 is present as a separating wall 242 which, in the operating state, separates the flowing fluid, which is also shown in FIGS. 13 and 14 by the arrows without reference signs in each case, from the receptacle 58. The thickness of the separating wall 242 is thereby dimensioned in such a way that the separating wall 242 on the one hand still has a sufficient stability and on the other hand allows a good thermal contact between the temperature sensor 59 and the fluid. Optionally, it is possible to account for or compensate for the temperature drop across the separating wall 242 (which preferably also consists of a plastic as a component of the drive housing 60) using a correction algorithm.

In the embodiment represented in FIG. 14, the hole 241 is designed such that it completely penetrates the bottom 24 of the measuring housing 60. A thermal coupling element 243 is arranged at the end of the hole 241 over which the fluid flows in the operating state, which closes the hole 241 and preferably closes it in a sealing manner. In the operating state, the thermal coupling element 243 is in direct physical contact with the fluid on one side and in direct physical contact with the temperature sensor 59 on the other side.

The thermal coupling element 243 preferably consists of a corrosion resistant metal that has a good thermal conductivity, or of another corrosion resistant material that has a good thermal conductivity. The thermal contact between the fluid and the temperature sensor 59 can be improved by the thermal coupling element 243.

The thermal coupling element 243 can be fixed in the bottom 24 of the measuring device 10 in various ways. For example, it can be fixed in the hole 241 by gluing or by a press-fit. It is also possible to overmold the thermal coupling element 243 with the plastic during the manufacture of the measuring device 10, which is preferably performed using an injection molding process. Optionally, a sealing element (not shown), such as an O-ring can be provided on the thermal coupling element 243.

Figure 15:
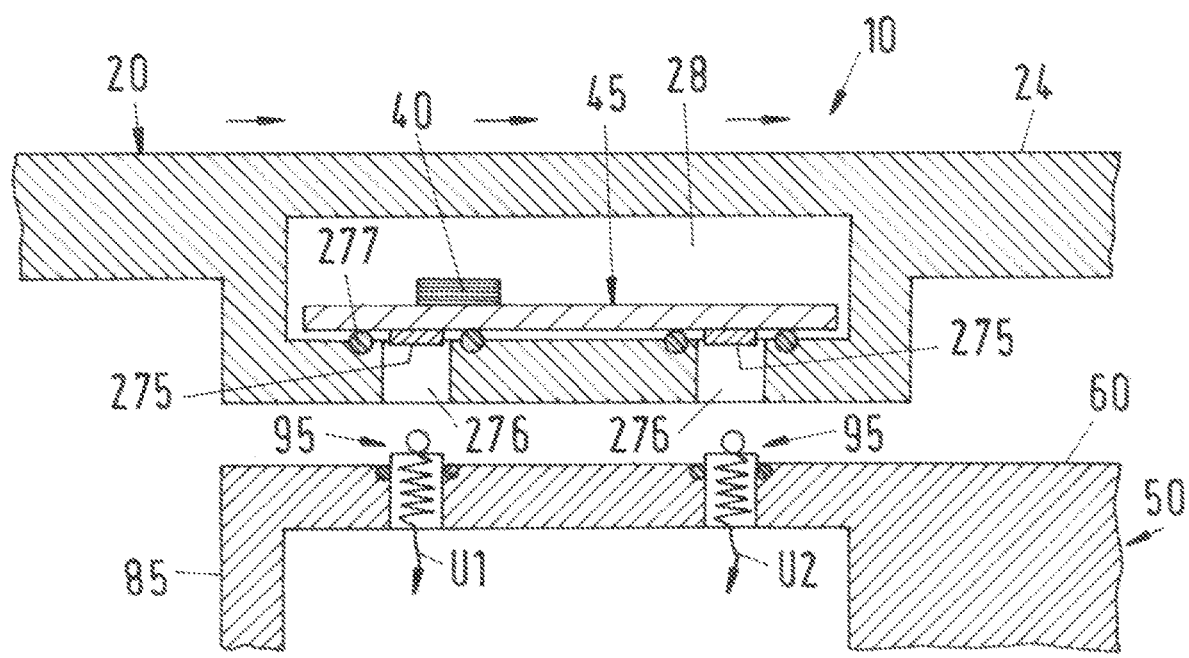
FIG. 15 illustrates a further possible embodiment for a signal connection enabling an electrical connection between the measuring device and the drive device.

In a representation analogous to FIG. 12, FIG. 15 shows a further embodiment for a signal connection which enables an electrical connection between the measuring device 10 and the drive device 50. However, the temperature sensor 49, which can of course also be provided in the embodiment represented in FIG. 15, is not represented in FIG. 15.

In the embodiment represented in FIG. 15, instead of the electrical contacts 27 in the measuring device 10 (FIG. 12), the storage PCB 45 includes electrical contact surfaces 275, each arranged over an opening 276 so that each spring contact 95 can contact one of the electrical contact surfaces 275. The storage PCB 45 can also be designed as a flexible PCB. The storage PCB 45 can be attached in a watertight manner in the cavity 28, for example, by gluing or press-fit technology, so that the fluid cannot get out of the measuring device 10 through the cavity 28. Furthermore, sealing elements 277, such as an O-ring in each case, can be provided around the openings 276.

Figure 16:
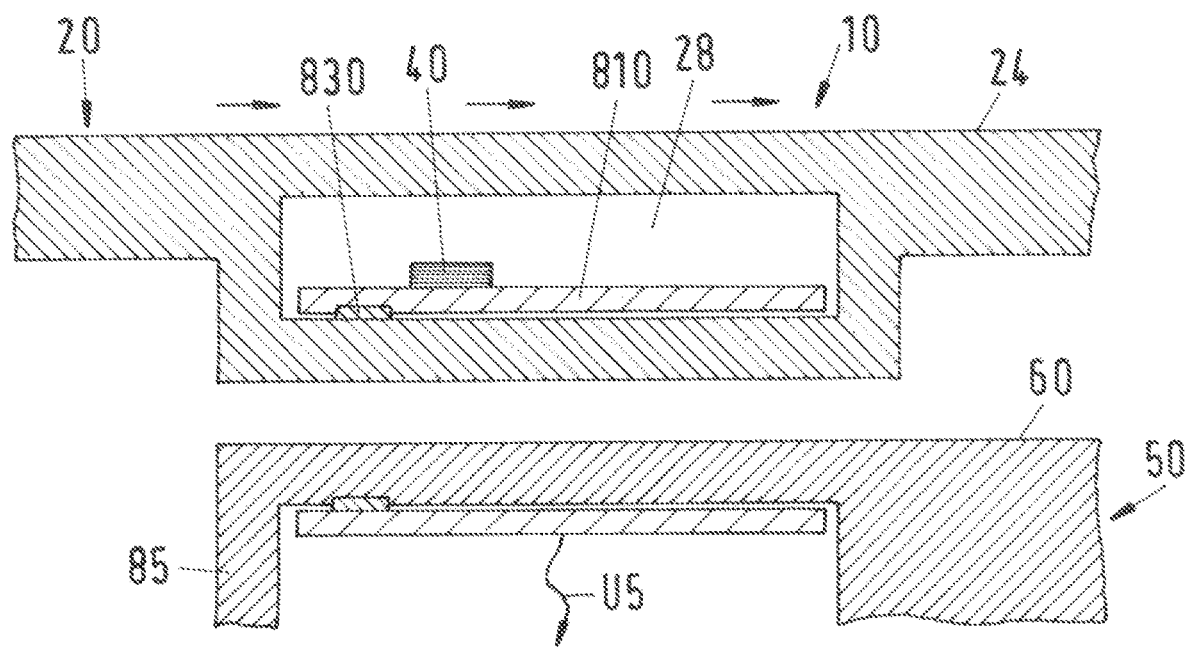
FIG. 16 illustrates an embodiment for the communication between the storage unit of the measuring device and the drive device.
Figure 17:
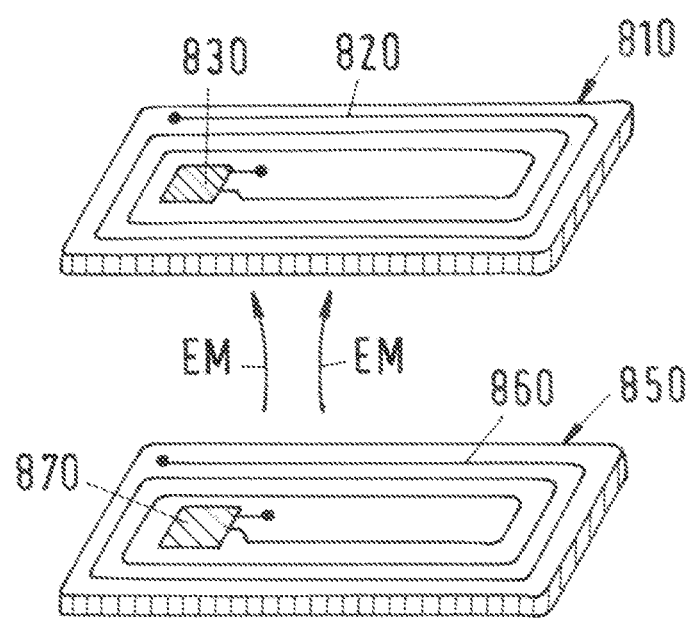
FIG. 17 illustrates the two components for the communication according to the embodiment in FIG. 16.

The communication between the storage unit 40 of the measuring device 10 and the control device 8 of the drive device 50 can also take place by RFID technology (RFID: Radio Frequency Identification). Such an embodiment is represented in FIG. 16. For better understanding, FIG. 17 also shows the two components for radio frequency identification.

A first antenna support 810 is provided in the measuring device 10, which supports a first antenna 820 and the storage unit 40 (not represented in FIG. 17), wherein the antenna 820 is connected to a passive transponder 830 which is arranged on the first antenna support 810.

A second antenna support 850 is provided in the drive device 50, which supports a second antenna 860 connected to an active transceiver 870 which is arranged on the second antenna support 850. The active transceiver 870 is signal-connected to the control device via a signal connection U5.

The passive transponder 830 and the active transceiver 870 communicate with each other in a manner known per se via electromagnetic fields EM.

The passive transponder 830 and the active transponder 870 are each arranged such that they are as close to each other as possible when the measuring device 10 and the drive device 50 are in the assembled state. By using a suitable EM field strength and shape of the antennas 820, 860, it can be achieved that only the directly adjacent passive transponder 830 is read out and no others in the close vicinity.

Figure 18:
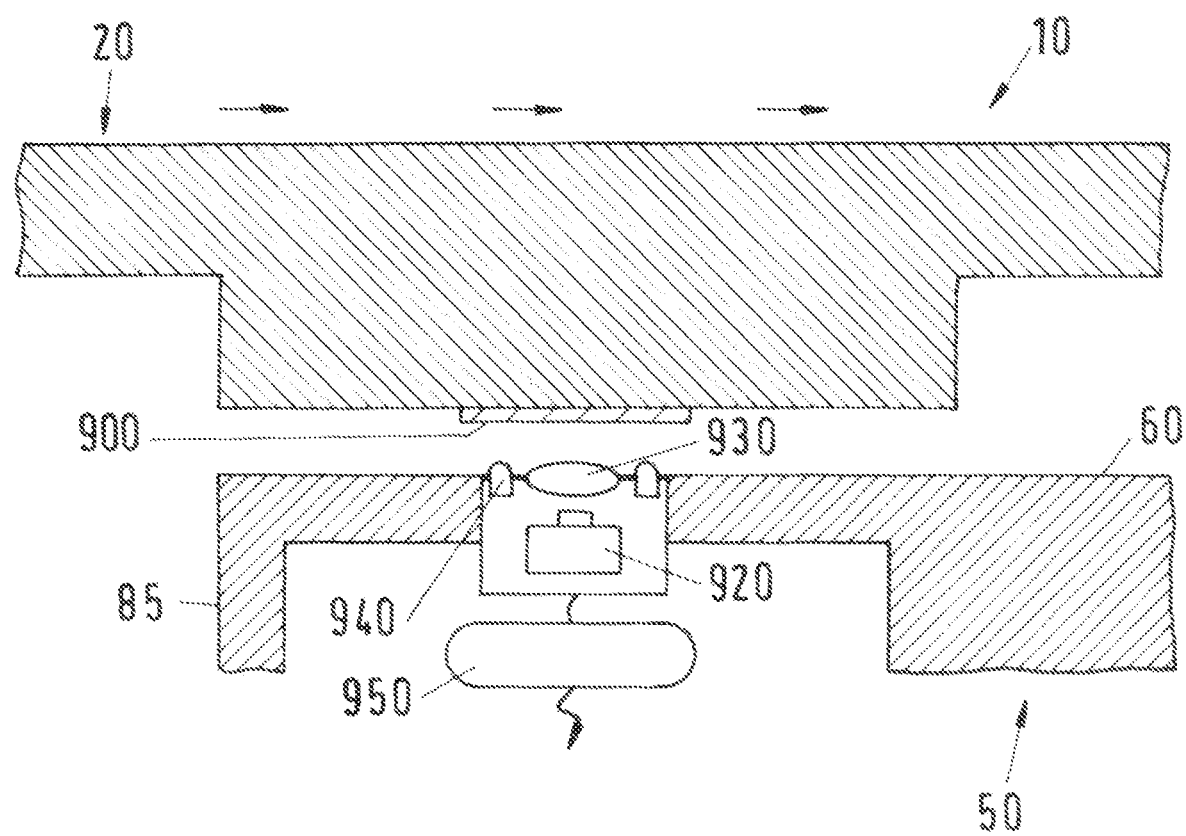
FIG. 18 illustrates a further embodiment for the communication between the storage unit of the measuring device and the drive device.
Figure 19:
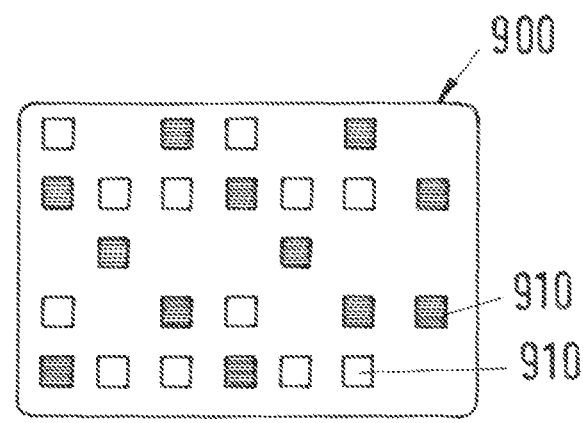
FIG. 19 illustrates a marking for the embodiment according to FIG. 18.

Another possibility to transmit calibration data or configuration parameters of a specific measuring device 10 to the storage reading unit 80 of the control device 8 of the drive device 50 is represented in FIG. 18 and in FIG. 19. In this embodiment, the measuring device 10 includes a tag 900 containing the specific information 910, i.e., for example the calibration data, for this measuring device 10. For example, the tag 900 is designed as a two-dimensional "bar code", such as a QR code. For better understanding, FIG. 19 shows an example of such a tag 900.

The tag 900 is visible from the outside or arranged visually accessible from the outside on the measuring device, namely on that side of the measuring device which faces the drive device 60 in the assembled state.

A camera 920 is provided in the drive device 50, which can capture the tag 900. This means that the tag 900 is arranged on the measuring device 10 in such a way that it is in the line of sight of the camera 920 in the assembled state, i.e., when the measuring device 10 is inserted into the drive device 50.

The camera 920 is signal-connected to a processing unit 950, which can be designed as a separate unit, or which can be integrated into the storage reading unit 80 of the control device 8. Optionally, a lens 930 and/or at least one illumination source 940 can be provided in the drive device 50 to ensure a reliable optical capture of the tag 900 by the camera 920 under all conditions. In particular, the illumination source 940 can be designed as an LED.

Figure 20:
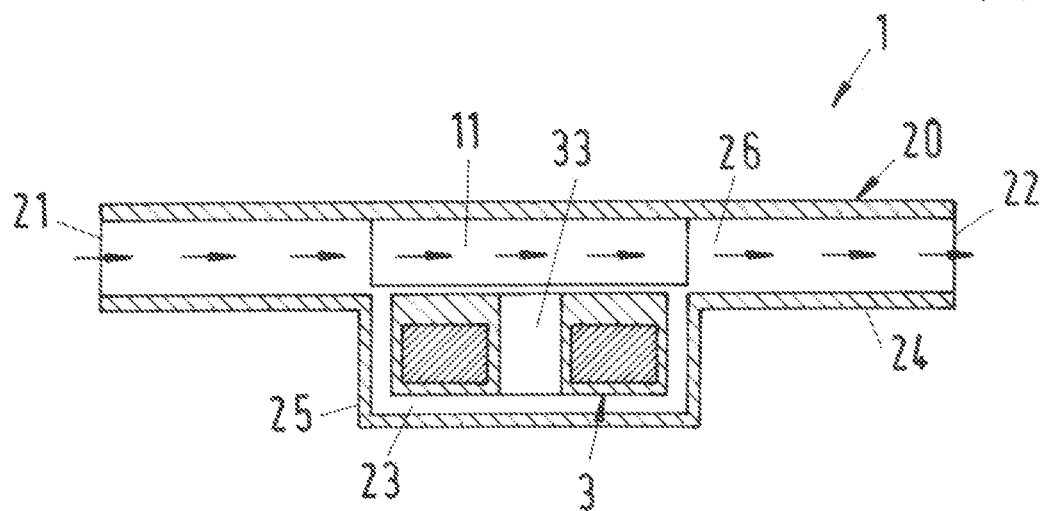
FIG. 20 illustrates a schematic sectional representation of a variant for the measuring device.

FIG. 20 shows in a schematic sectional representation a variant for the measuring device 10. This variant is suitable for all embodiments described up to now or can be combined with all embodiments and forms of embodiments.

Figure 21:
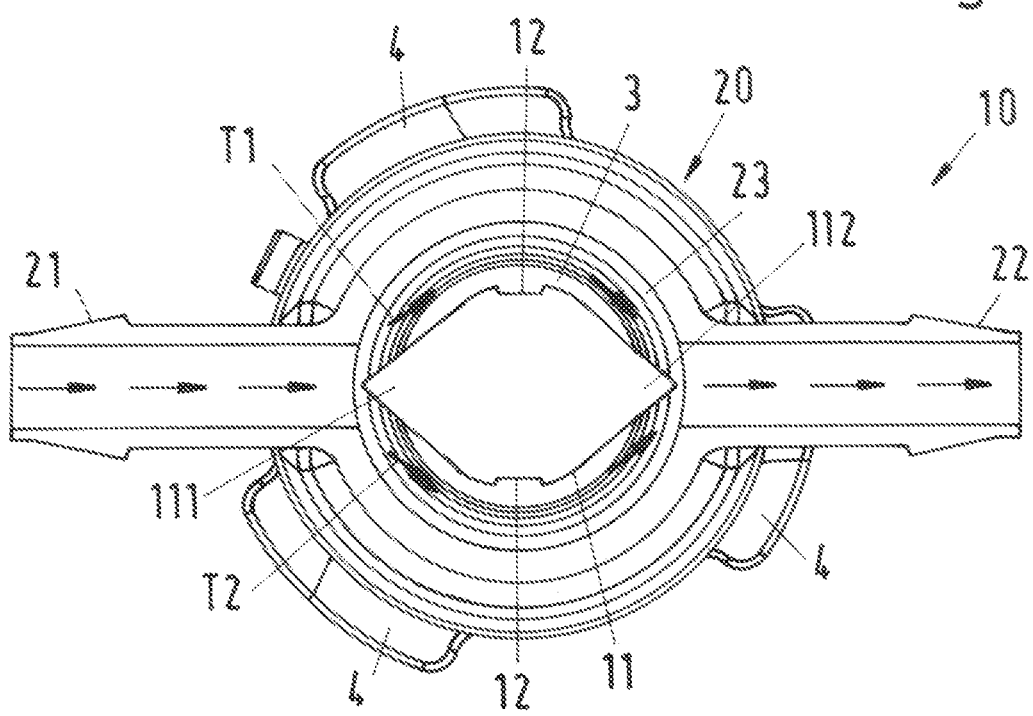
FIG. 21 illustrates a top view onto the variant from FIG. 20.
Figure 22:
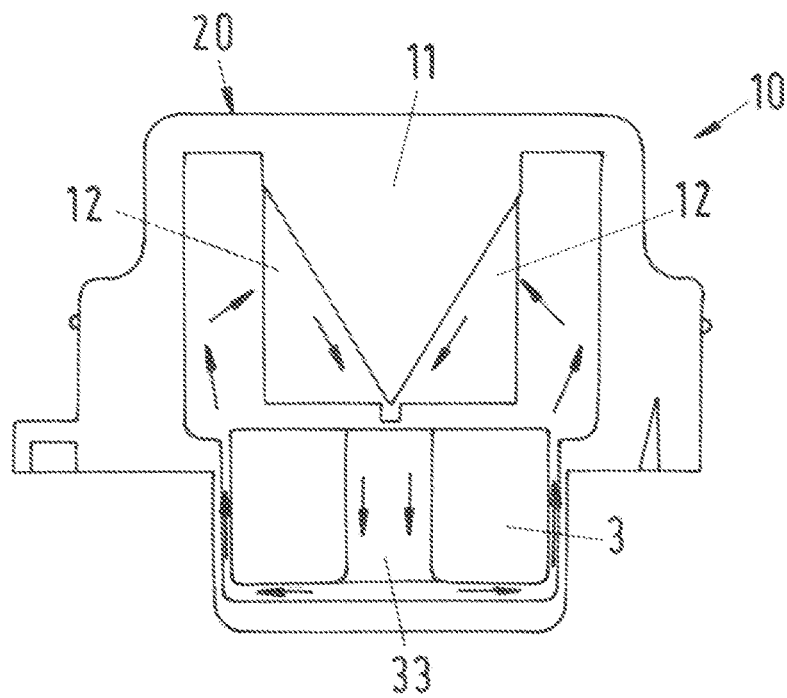
FIG. 22 illustrates a sectional representation of the variant from FIG. 20.
Figure 23:
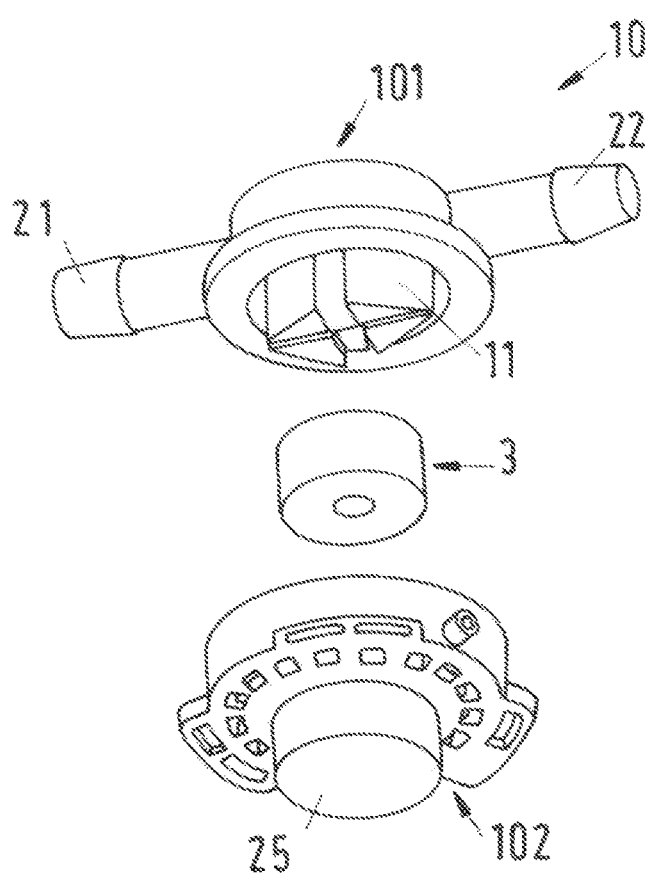
FIG. 23 illustrates an exploded representation of the variant from FIG. 20.

For better understanding, FIG. 21 shows a top view onto this variant, wherein the variant is represented open at the top so that the measuring chamber 23 is visible. FIG. 22 shows a sectional representation of the variant in a section along the axial direction A, wherein the direction of view is directed from the inlet 21 into the main flow connection 26. FIG. 23 shows a perspective exploded representation of the variant.

In the variant for the measuring device 10, a flow guiding element 11 is disposed in the main flow connection 26, which is arranged centrally above the rotor 3, and which is designed to divide the fluid into a first partial flow T1 and into a second partial flow T2, in such a way that the flow guiding element 11 between the inlet 21 and the outlet 22 has the first partial flow T1 flowing around it on one side and the second partial flow T2 flowing around it on the other side. Here, the flow guiding element 11 is preferably designed such that it divides the fluid as symmetrically as possible into the two partial flows T1 and T2.

As shown in particular by the top view in FIG. 21, the flow guiding element 11 has two end portions 111, 112, namely a first end portion 111 which faces the inlet 21 and which extends to just before the inlet 21, and a second end portion 112 which faces the outlet, and which extends to just before the outlet 22. The first end portion 111 is designed to widen in the radial direction in such a way that the first end portion 111 becomes widened when viewed in the radial direction as one moves from the inlet 21 toward the outlet 22. The second end portion 112 is designed to taper in a radial direction in such a way that the second end portion 112 becomes narrower when viewed in a radial direction as one moves from the inlet 21 toward the outlet 22. Due to this embodiment, the fluid is divided into the two partial flows T1, T2 immediately downstream of the inlet 21, when viewed in the direction of flow, and these two partial flows T1. T2 are combined again immediately upstream of the outlet 22.

Due to the flow guiding element 11, which covers the central area of the rotor 3, the fluid is thus divided in the operating state into the two partial flows T1 and T2, which substantially only flow over the periphery of the surface of the rotor 3. Thus, by the flow guiding element 11, rotational flows in the main flow connection 26 are prevented or at least drastically reduced. Such rotational flows can have a negative effect because they flow against the main flow on one side at the surface of the rotor 3 and flow in the same direction as the main flow on the other side. Hereby, asymmetric friction effects can result, which can have a negative effect on the measurement of the viscosity.

A further advantage of the embodiment with the flow guiding element 11 is that it occupies a significant space in the main flow connection 26. This has the advantage that the wet volume, by which is meant the area of the measuring device 10 which is filled with the fluid, or through which the fluid flows, is reduced. This is a particularly important aspect if the fluid is a very valuable or expensive fluid.

Another preferred measure is that the flow guiding element 11 has a plurality of side channels 12 which divert a portion of the fluid from the main flow connection 26 in the axial direction A toward the rotor 3. Due to this measure, the secondary flow can be amplified, which is the flow of the fluid that flows around the rotor 3 and is therefore a significant factor in determining the viscosity.

The secondary flow is represented in FIG. 22 by the arrows without reference signs. In FIG. 22, the design of the side channels 12 can also be clearly seen. FIG. 22 shows a section in the axial direction A through the measuring device 10, wherein the section is made midway between the inlet 21 and the outlet 22. The view is directed from the inlet 21 to the measuring chamber 23. In this representation of FIG. 22, each side channel 12 has a triangular profile, wherein the depth of each side channel 12 measured in the radial direction increases as one moves toward the rotor 3 in the axial direction.

A part of the fluid is diverted through the side channels 12 as a secondary flow from the radial direction into the axial direction and flows primarily through the central opening 33 of the rotor 3 due to the triangular profile of the side channels 12. After flowing through the central opening 33, the secondary flow flows along the underside of the rotor 3 and is then guided between the wall delimiting the protuberance 25 and the shell surface of the rotor 3 in axial direction A back into the main flow connection 26.

The secondary flow of the fluid is increased by the flow guiding element 11 with the side channels 12, which improves the fluid exchange at the rotor 3.

Preferably, the measuring device 10 is composed of three main components (see FIG. 23), namely the rotor 3, which comprises the magnetically effective core 31 as well as the sheath 32, an upper part 101, which comprises the upper part of the measuring housing 20, the inlet 21, the outlet 22 and the flow guide body 11, and a lower part 102, which comprises the bottom 24 with the protuberance 25 and the measuring chamber 23.

In particular, the upper part 101 and the lower part 102 are preferably manufactured by an injection molding process and subsequently assembled by methods known per se after the rotor 3 has been placed in the measuring chamber 23. Welding methods, such as laser welding or infrared welding, or gluing methods are particularly suitable as methods for assembling the upper part 101 and lower part 102.

Since the viscometer 1 according to embodiments of the invention enables a very simple, precise and easy-to-handle determination of the viscosity of a fluid, it is also particularly suitable for determining characteristic values, properties or states of a fluid which can be determined with the help of the viscosity of the fluid. One important of these values is the concentration of a component in a fluid. Therefore, a method for determining a concentration of a component in a fluid is further proposed by an embodiment of the invention, characterized by the following steps:

Providing a viscometer 1 which is designed according to an embodiment of the invention,
Providing a relationship between the concentration of the component in the fluid and the viscosity of the fluid,
Determining the viscosity of the fluid by the viscometer 1,
Determining the concentration from the relationship between the concentration and the viscosity.

Such concentration determinations also play an important role in the biotechnology and pharmaceutical industries in particular. Here, the concentrations of proteins in a bioreactor or in a cell broth, for example, can be mentioned as examples.

Figure 24:
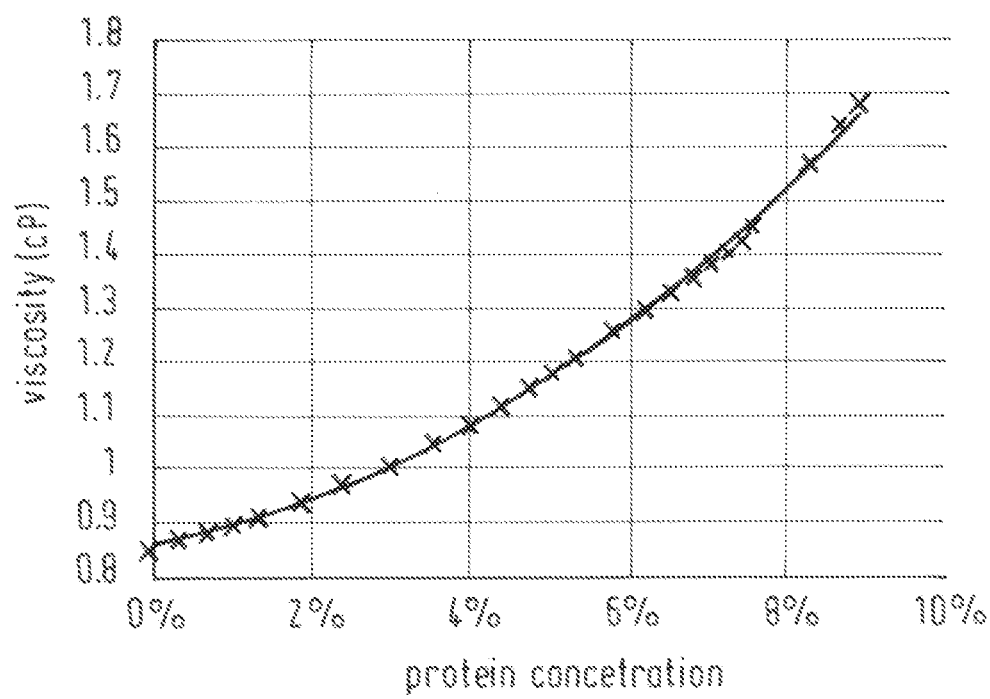
FIG. 24 illustrates a diagram showing the relationship between the viscosity and the concentration of a component in a fluid.

With exemplary character, FIG. 24 shows the relationship between the concentration of a protein in a fluid plotted on the horizontal axis and the viscosity of the fluid plotted on the vertical axis. It can be seen very clearly that because of this relationship between concentration and the viscosity, a viscosity measurement is very well suited to determine the protein concentration in a fluid.

Figure 25:
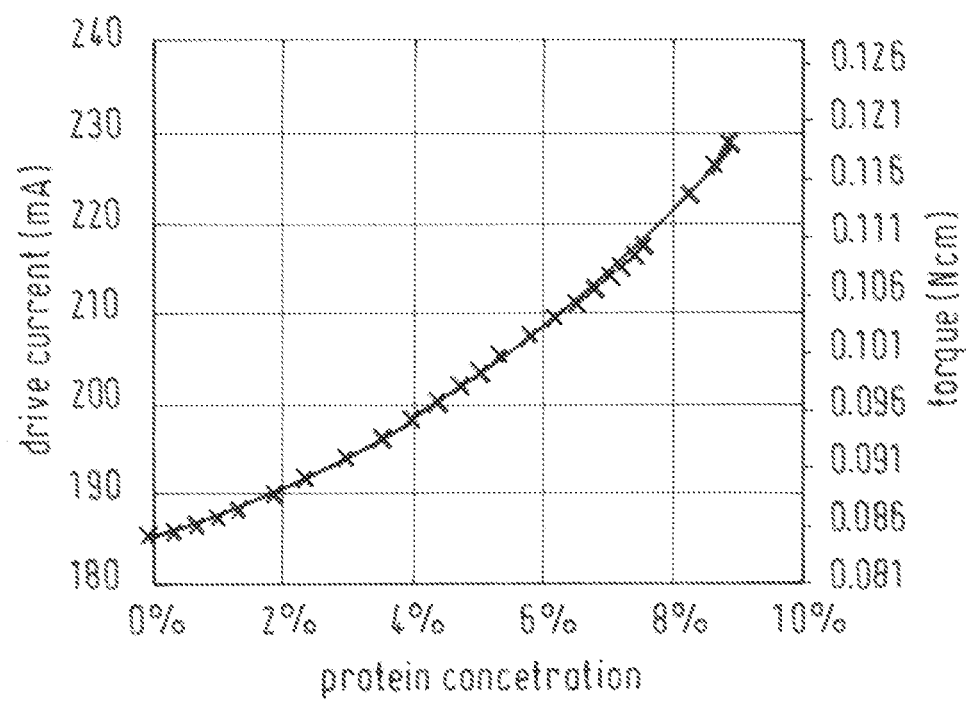
FIG. 25 illustrates a diagram showing the relationship between the drive current or torque and the concentration of a component in a fluid.

Since the viscosity in the viscometer according to an embodiment of the invention is preferably determined by the drive current required to drive the rotation of the rotor 3, the relationship between the concentration of the protein (horizontal axis) and the drive current (left vertical axis) or the torque (right vertical axis) required to drive the rotation of the rotor 3 is also shown in FIG. 25. Here again, it can be seen that this relationship enables a very good determination of the concentration of a protein in a fluid with the help of the viscometer 1 according to an embodiment of the invention.

An important application is, for example, the determination of the immunoglobulin (antibody) concentration in a fluid. Especially the determination of the concentration of immunoglobulins plays an important role in modern diagnostics, in biotechnology and in the development of vaccines and drugs. The viscometer 1 according to an embodiment of the invention is very suitable for such applications.

Since each immunoglobulin shows a characteristic, concentration-dependent viscosity, the immunoglobulin concentration can be determined from the viscosity, if the class of immunoglobulin (IgG, IgM, IgA, IgD, IgE) and subclass (e.g., igG1, igG2, igG3, igG4) of the immunoglobulins are known or, conversely, to conclude the type of immunoglobulins if the concentration is known. In the case of mixtures of two proteins (e.g., igG1 and igG4) and knowledge of the total protein concentration on the basis of another physical value such as the density of the liquid, the propagation speed of ultrasound in the liquid, the absorption of light at one or more wavelengths or the refractive index of light at one or more wavelengths, etc., the mixing ratio or the relative proportion of the two proteins can be determined via the viscosity.

It goes without saying that the mixing ratios of other liquids of different viscosities can also be determined by the same method.

Since the relationship between the viscosity and the protein concentration in a fluid is generally dependent on the temperature, the relationship between the concentration of the protein in the fluid and the viscosity of the fluid is preferably determined for several temperatures and then stored in the control device 8, for example in the form of a lookup table, as a three-dimensional characteristic curve field with the dimensions concentration, viscosity, temperature. Of course, it is also possible to carry out the determination of the concentration on an external data processing system into which the measurement results or measured values of the viscometer 1 are fed.

As an example of the temperature dependence of the relationship between concentration and viscosity, the relationship between the concentration of immunoglobulin G1 (igG1) (vertical axis) in a fluid and the viscosity of the fluid (horizontal axis) for five different temperatures is represented in FIG. 26. The curve K1 shows the relationship for a temperature of 5° C. The curve K2 shows the relationship for a temperature of 10° C. The curve K3 shows the relationship for a temperature of 15° C. The curve K4 shows the relationship for a temperature of 20° C. The curve K5 shows the relationship for a temperature of 25° C.

According to the method according to an embodiment of the invention, such a relationship as represented in FIG. 26 can serve, for example, for on-line monitoring of the protein concentration in various bioprocessing methods, in particular in downstream bioprocessing methods. Examples of downstream bioprocessing methods in which monitoring of the protein concentration or also directly of the viscosity can be useful are, for example, cross-flow or crossflow filtration methods, in particular ultrafiltration and diafiltration methods, which serve for purification and/or concentration of the biotechnologically produced active ingredients. In such cross-flow filtration methods, the continuous monitoring of the viscosity can serve to determine other process parameters, such as the optimum transmembrane pressure and the tangential flow, and to adapt them to the process progress. The indirect determination of the protein concentration is an important indicator of the process progress and for the process yield.

In centrifugation separation processes, in particular in continuous centrifugation processes, the viscosity also provides decisive information about the process progress or the process constancy.

In chromatography processes, in particular in continuous chromatography processes, the viscosity and the protein concentration obtained from it can provide information about the process yield and the condition of the chromatography columns or the chromatography membranes.

Since a large number of different protein solutions and other liquids are processed in bioprocessing plants, the viscometer 1 according to an embodiment of the invention can further comprise an additional storage or be designed for communication with an external storage. Many different data sets can be stored in this storage, which describe the relationship between viscosity, temperature, and concentration of various liquids, in particular protein solutions, analogous to the relationship between viscosity, temperature and concentration of the immunoglobulin G1 (igG1) represented in FIG. 26. For example, the data sets can be stored as support values in lookup tables, wherein the temperature and the viscosity together can make up the lower and upper "bits" of a storage address, and wherein the concentration value is stored as a support value in the corresponding storage cell.

These data sets can be stored either directly in a data storage of the viscometer 1 according to an embodiment of the invention, which is provided for example in the control device 8, or in a separate evaluation unit 304 (e.g., FIG. 27) connected to the viscometer.

Of course, it is also possible to store such data sets on a cloud storage and to make the data sets accessible to a large number of viscometers 1 according to an embodiment of the invention or evaluation units 304 via an internet connection. In doing so, the data sets can be continuously supplemented and improved.

Furthermore, it is possible that the data sets are stored on chip cards, removable flash memory storages or other internal or external storage media. Inter alia, it is also possible to store the data in the storage unit 40 of the measuring device 10 together with the calibration data of the measuring device 10.

In this case, the measuring device 10 is preferably configured for the concentration measurement of one liquid or of several liquids. In particular, all required calibration data are stored in the storage unit 40 of the measuring device.

Together with at least one of the mentioned data storages and the data sets stored therein, the viscometer 1 according to an embodiment of the invention can in particular also be used or employed as a concentration measuring device for various liquids, in particular for protein solutions.

FIG. 27 shows a schematic representation of a first embodiment of a method according to an embodiment of the invention, in which a protein concentration is determined. In this embodiment of the method according to the invention, the viscometer 1 is thus used as a concentration measuring device.

In this first embodiment, at least a protein concentration in a liquid is determined. The viscometer 1 is typically integrated into a fluid system 400, which can comprise pumps, feeders, as well as bioprocessing equipment, such as filter devices, centrifuges, chromatography equipment, bioreactors, and/or mixing equipment, which is not represented in detail in FIG. 27, but only as the fluid system 400.

An actual viscosity VA of the liquid is determined by the viscometer 1 continuously or at predeterminable time intervals, which is transmitted to an evaluation unit 304. The temperature T of the liquid is determined by the temperature sensor 49 and/or 59. Even though the temperature T is preferably determined with a temperature sensor arranged in the viscometer 1, i.e. for example with the temperature sensor 49 in the measuring device 10 or with the temperature sensor 59 in the drive device 50, it is also possible to determine the temperature T with an external temperature measuring device that is not integrated in the viscometer 1. As described above, the relationships between the temperature T, the viscosity and the concentration are stored in the evaluation unit 304 for at least one or for several liquids, as shown exemplarily in FIG. 26 for the immunoglobulin igG1. The evaluation unit 304 then determines from the viscosity and the temperature T at least a protein concentration CP of a protein or the concentration of other substances, which can be dissolved in the liquid or can be present as suspensions of microparticles and nanoparticles or of cells. As already described, the relationships between the temperature T, the viscosity and the concentration can also be stored directly in a storage of the viscometer 1 or in an external storage that can be accessed by the viscometer 1. In this case, the control device 8 of the viscometer 1 can take over the function of the evaluation unit 304 and supplement the viscometer 1 with the function of a concentration measuring device.

As already mentioned, the viscometer 1 when used as a concentration measuring device, respectively the method according to an embodiment of the invention for determining a concentration of a component in a fluid, is not limited to the measurement of protein concentrations in liquids.

Another application example is the determination of the cell density in a cell suspension (which could also be designated as cell concentration). As an example of the relationship between the cell density in a cell suspension and the viscosity of the cell suspension, the relationship between the cell density of *Escherichia coli* bacteria (*E-Coli* bacteria) in a cell suspension and the viscosity of this cell suspension (vertical axis) is shown in FIG. 28.

Such *E-coli* cell cultures are used, for example, in bioreactors to produce insulin, a high-molecular-weight protein. As a representative value for the cell density, the optical density of the cell suspension at a light wavelength of 600 nm is plotted on the horizontal axis in FIG. 28, i.e., FIG. 28 shows the relationship between the viscosity of the cell suspension and the optical density at a light wavelength of 600 nm, the so-called OD600 value. Since the relationship between the OD600 value and the cell density for *E-coli* cell cultures is linear to a very good approximation and is additionally well known (an OD600 value of 1 corresponds to about $8*10^8$ cells per milliliter), the OD600 value is often indicated in biotechnology instead of the cell density. Therefore, in FIG. 28, the maximum OD600 value of 220 corresponds approximately to a cell density of $220*8*10^8=1.76*10^{11}$ cells per milliliter. This is close to the upper limit of cell densities that can be achieved with *E-coli* cell cultures.

With the help of the method described above, the function of a cell density measurement device can be realized in a manner analogous to the function of a concentration measuring device by the viscometer 1 and the evaluation unit 304, in which the relationship between the viscosity of the cell suspension and the OD600 value shown in FIG. 28 is stored as a data set.

However, the determination of cell density by the viscometer 1 is usually less accurate compared to the determination by optical cell density measurement devices. As shown in FIG. 28, the viscosity change of the bioreactor medium (cell suspension) is only 0.75 mPa s over the entire cell density range. The viscosity of the bioreactor medium can change by up to 20% due to temperature influences and the changing composition of the medium. Thus, if the cell density is determined from the viscosity change, the result is a less accurate measurement compared to optical methods as a consequence of the low resolution and the external influences, which cannot all be completely compensated. In animal cell cultures, the measurement can become even less accurate due to the lower cell densities.

Thus, the practical significance of the determination of the cell density by the viscometer 1 is limited. In contrast, the change in viscosity to be expected in the *E-coli* cell culture with increasing cell density can be determined from the OD600 value with very good resolution and high accuracy from the relationship between the viscosity and the OD600 value represented in FIG. 28. In this case, it is advantageous that the influence of the cell density on the viscosity is small and thus the cell density-viscosity curve is relatively flat.

In contrast to the dependence of the viscosity of the cell broth on the cell density, the dependence of the viscosity on the protein concentration in the cell broth is much stronger. By knowing the viscosity contribution of the cell density to the total viscosity of the cell broth, the extracellular protein concentration can be determined in bioreactors, provided that the viscosity of the cell broth and the expected protein composition are known.

For this purpose, the viscosity of the cell broth is measured, the influence of the cell concentration on the viscosity is determined via the OD600 value and the relationship between the viscosity and the OD600 value represented in FIG. 28, and this is offset against the viscosity of the cell broth. This method can be particularly interesting for determining the concentration of so-called "leakage proteins", which are released from the cultured cells into the cell broth by cell lysis (breakage of the cell membrane). The concentration of these leakage proteins is, inter alia, an indicator of the proportion of productive cells, cell viability, and provides information on whether there are still sufficient productive cells to produce the desired active ingredient. Certain leakage proteins can have a toxic effect on cells, and thus accelerate cell death. Such toxic proteins must later be separated from the active ingredient in so-called "downstream processing" by expensive processes (e.g., chromatography). Therefore, it is important to be able to determine as precisely as possible the correct time when the cell culture should be terminated. The concentration of the leakage proteins is an important indicator for this.

FIG. 29 shows a schematic representation of a second embodiment of the method according to the invention. This second embodiment serves to measure the concentration of extracellular proteins, in particular leakage proteins, in bioreactors. In this second embodiment, at least a protein concentration in a cell broth is determined. In FIG. 29, a bioreactor 300 is shown, in which a cell broth is contained for a biological or a biotechnological process. The bioreactor 300 is typically integrated into a fluid system, which can comprise filtering devices, pumps, feeders, for example for a nutrient solution, withdrawal devices, which is not shown in detail in FIG. 29. The viscometer 1 is designed for an inline measurement, i.e., the measuring device 10 of the viscometer 1 is continuously flown through by the cell broth. By the viscometer 1, the actual viscosity VA of the cell broth is determined continuously or at predeterminable time intervals, which is transmitted to a correction unit 301. The temperature T of the cell broth is determined by the temperature sensor 49 and/or 59. Even though the temperature T is preferably determined with a temperature sensor arranged in the viscometer 1, i.e., for example with the temperature sensor 49 in the measuring device 10 or with the temperature sensor 59 in the drive device 50, it is also possible to determine the temperature T with an external temperature measuring device that is not integrated in the viscometer 1.

Furthermore, an actual cell density ZD in the cell broth is determined in a measuring device 302. The cell density ZD is preferably determined photometrically. As already described, it is common to characterize the cell density in a biological fluid, i.e., here in the cell broth, by the OD600 value, since it can be easily measured and correlates well with the cell density. The OD600 value indicates the optical density of the cell broth at a light wavelength of 600 nm. The actual cell density ZD can then be determined from this.

In a correction module 303, a correction value K for the viscosity at the temperature T is determined on the basis of a reference value for the relationship between the cell density ZD or the OD600 value and the viscosity for the temperature T measured. The correction value K is transmitted to the correction unit 301. For example, the relationship between the cell density or the OD600 value and the viscosity in the fresh cell soup can be used as a reference value in the correction module 303. The term "fresh cell soup" refers to that cell soup in which there are still no or only low concentrations of extracellular proteins and no or only a few proteins that pass into the cell broth when the cells are destroyed or burst open (leaked protein). In practice, the time period during which the cell soup can be designated as fresh according to the above definition varies with the type of cells grown and the type of cell culture. For batch cultures of *E-coli* bacteria, the cell soup can only be designated as "fresh" for approximately 24 to 36 hours and used to determine the reference value. In the case of cell cultures of animal cells in perfusion bioreactors or even in the case of fed-batch cell cultures, the cell soup can sometimes be designated as "fresh" for several days according to the above definition.

In the correction unit 301, the actual viscosity VA is corrected by the correction value K and a corrected viscosity KV is determined. For example, the correction value K is subtracted from the actual viscosity VA to determine the corrected viscosity KV in this way. For the temperature, the corrected viscosity KV thus represents the value of the viscosity considering the actual cell density ZD in the cell broth. The corrected viscosity KV is fed to the evaluation unit 304, in which such relationships between the temperature T, the viscosity and the concentration are stored, as shown by way of example in FIG. 26. The evaluation unit 304 then determines at least a protein concentration CP of an extracellular protein in the cell soup from the corrected viscosity KV and temperature T.

What is claimed is:

1. A viscometer for inline determination of the viscosity of a fluid, comprising:
   a drive device;
   a measuring device comprising a measuring housing with an inlet and with an outlet for the fluid, and a measuring chamber in which a rotor having a ring-shaped or disk-shaped magnetically effective core is provided, the drive device comprising a drive housing in which a stator is arranged, the stator cooperating with the rotor as an electromagnetic rotary drive, has and having a plurality of coil cores, each coil core being delimited by an end face, and carrying a concentrated winding, the stator being a bearing and drive stator with which the rotor is magnetically driven without contact about an axial direction and magnetically levitated without contact with respect to the stator during operation; and
   a control device configured to actuate the stator and determine the viscosity based on an operating parameter of the electromagnetic rotary drive disposed in the drive housing,
   the measuring device is designed to be inserted into the drive device such that the end faces of the coil cores are arranged around the magnetically effective core of the rotor, and the measuring housing configured to be detachably connected to the drive housing so that the measuring housing and the drive housing are fixable relative to each other and separable from each other.

2. The viscometer according to claim 1, wherein the electromagnetic rotary drive is a temple motor, and each coil core comprises a bar-shaped longitudinal leg extending from a first end in the axial direction to a second end, and a transverse leg arranged at the second end of the longitudinal leg and which extends in a radial direction that is perpendicular to the axial direction, and for each coil core, the transverse leg is delimited by one of a respective end face, and the concentrated winding is arranged the longitudinal leg and surrounds the longitudinal leg.

3. The viscometer according to claim 1, wherein the measuring housing is configured to be fixed to the drive housing or detached from the drive housing by a rotation relative to the drive housing and about the axial direction.

4. The viscometer according to claim 1, wherein the drive device comprises a connecting device configured to be rotatable with respect to the drive housing between an open position and a closed position, the measuring device is configured to be inserted into the drive device and separated from the drive device when the connecting device is in the open position, and the measuring housing and the drive housing are fixed relative to each other when the connecting device is in the closed position.

5. The viscometer according to claim 1, wherein the measuring device comprises a storage unit in which calibration data for the measuring device are stored, and the drive device comprises an interface via which data from the storage unit is configured to be transmitted to the control device.

6. The viscometer according to claim 1, wherein the magnetically effective core of the rotor comprises a permanent magnet to generate a rotor magnetic field, and the drive device comprises a magnetic field sensor configured to determine the rotor magnetic field.

7. The viscometer according to claim 6, further comprising a radial magnetic field sensor configured to determine a radial component of the rotor magnetic field.

8. The viscometer according to claim 6, further comprising a radial magnetic field sensor configured to determine a radial component of the rotor magnetic field and an axial magnetic field sensor configured to determine an axial component of the rotor magnetic field.

9. The viscometer according to claim 1, wherein the measuring device comprises a temperature sensor configured to determine a temperature of a fluid in the measuring device.

10. The viscometer according to claim 1, where the measuring chamber is a protuberance in a bottom of the measuring housing, and, with respect to a normal position of use, a main flow connection for a fluid is provided in the axial direction above the measuring chamber between the inlet and the outlet, and the fluid is configured to flow from the inlet to the outlet through the main flow connection.

11. The viscometer according to claim 10, wherein a flow guiding element is disposed in the main flow connection, is arranged centrally above the rotor, and divides the fluid into a first partial flow and into a second partial flow such that the flow guiding element between the inlet and the outlet has the first partial flow flowing therearound on one side and the second partial flow flowing therearound on an other side.

12. The viscometer according to claim 11, wherein the flow guiding element has a plurality of side channels which divert a portion of the fluid from the main flow connection in the axial direction towards the rotor.

13. The viscometer according to claim 1, wherein the drive device is a reusable device for multiple use, and the measuring device is a single-use device for single use.

14. A single-use device for single use, wherein the single-use device is the measuring device for the viscometer according to claim 13.

15. A method for determining a concentration of a component in a fluid, the method comprising:
    providing the viscometer according to claim 1;
    providing a relationship between the concentration of the component in the fluid and a viscosity of the fluid;
    determining the viscosity of the fluid by the viscometer; and
    determining the concentration from a relationship between the concentration and the viscosity.

16. The method according to claim 15, further comprising determining a protein concentration in a cell broth, including determining an actual viscosity of the cell broth with the viscometer, determining an actual cell density in the cell broth, determining a correction value for the viscosity based on a reference value for a relationship between the cell density and the viscosity, determining a corrected viscosity from the actual viscosity and the correction value, and determining the protein concentration in the cell broth from the corrected viscosity and the relationship between the concentration and the viscosity.

17. The method according to claim 15, further comprising determining a protein concentration in a cell broth, including determining an actual viscosity of the cell broth with the viscometer, photometrically determining an actual cell density in the cell broth, determining a correction value for the viscosity based on a reference value for a relationship between the cell density and the viscosity, determining a corrected viscosity from the actual viscosity and the correction value, and determining the protein concentration in the cell broth from the corrected viscosity and the relationship between the concentration and the viscosity.

* * * * *